United States Patent
Abe

(10) Patent No.: US 11,304,681 B2
(45) Date of Patent: Apr. 19, 2022

(54) ULTRASONIC DIAGNOSTIC APPARATUS AND IMAGE PROCESSING METHOD

(71) Applicant: Toshiba Medical Systems Corporation, Otawara (JP)

(72) Inventor: Yasuhiko Abe, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 744 days.

(21) Appl. No.: 15/428,381

(22) Filed: Feb. 9, 2017

(65) Prior Publication Data

US 2017/0252011 A1 Sep. 7, 2017

(30) Foreign Application Priority Data

Mar. 3, 2016 (JP) .............................. JP2016-041100
Dec. 19, 2016 (JP) .............................. JP2016-245637

(51) Int. Cl.
*A61B 8/08* (2006.01)
*A61B 8/00* (2006.01)
*A61B 5/349* (2021.01)

(52) U.S. Cl.
CPC .......... *A61B 8/5223* (2013.01); *A61B 8/0883* (2013.01); *A61B 8/4444* (2013.01);
(Continued)

(58) Field of Classification Search
CPC ......... A61B 8/08; A61B 8/5223; A61B 8/461; A61B 8/4483; A61B 8/488; A61B 8/4444; A61B 8/0883; A61B 5/0452; A61B 5/349
(Continued)

(56) References Cited

U.S. PATENT DOCUMENTS 6,447,450 B1 * 9/2002 Olstad ................. A61B 5/0456
600/437
2003/0191403 A1 * 10/2003 Zhou .................... A61B 5/0464
600/515

(Continued)

FOREIGN PATENT DOCUMENTS

JP 2010-227568 10/2010
JP 2012-005708 A 1/2012
(Continued)

OTHER PUBLICATIONS

Japanese Office Action dated Sep. 8, 2020, issued in Japanese Patent Application No. 2016-245637.
(Continued)

*Primary Examiner* — Oommen Jacob
(74) *Attorney, Agent, or Firm* — Oblon, McClelland, Maier & Neustadt, L.L.P.

(57) ABSTRACT

An ultrasonic diagnostic apparatus according to an embodiment includes a processing circuitry. With respect to pieces of image data of a plurality of cross sections passing through the heart of a subject that have been collected by ultrasonically scanning each of the cross sections for a period of at least one heart beat, the processing circuitry performs tracking processing including two-dimensional pattern matching to generate pieces of analysis information in each of which a cardiac wall motion of the heart in each section is analyzed. The processing circuitry matches time phases of the pieces of analysis information of the cross sections and maps the pieces of analysis information of the cross sections with the matched time phases on a predetermined polar coordinate system to generate a polar coordinate display image. The processing circuitry causes display of the polar coordinate display image.

13 Claims, 14 Drawing Sheets

(52) U.S. Cl.
CPC ............ *A61B 8/4483* (2013.01); *A61B 8/461* (2013.01); *A61B 8/488* (2013.01); *A61B 5/349* (2021.01)

(58) Field of Classification Search
USPC .................................................. 600/437, 407
See application file for complete search history.

(56) References Cited

U.S. PATENT DOCUMENTS

| | | | | |
|---|---|---|---|---|
| 2005/0069081 | A1* | 3/2005 | Kokubun | A61B 6/032 378/15 |
| 2005/0245812 | A1* | 11/2005 | Kim | A61B 5/055 600/410 |
| 2007/0066886 | A1* | 3/2007 | Kuhara | G01R 33/5673 600/413 |
| 2007/0276239 | A1* | 11/2007 | Rafter | A61B 8/06 600/437 |
| 2007/0276275 | A1* | 11/2007 | Proctor | A61B 5/02405 600/513 |
| 2008/0285819 | A1* | 11/2008 | Konofagou | A61B 8/08 382/128 |
| 2009/0043200 | A1* | 2/2009 | Abe | A61B 8/08 600/443 |
| 2009/0198133 | A1* | 8/2009 | Kawagishi | A61B 8/08 600/443 |
| 2010/0041992 | A1* | 2/2010 | Ohuchi | A61B 8/08 600/443 |
| 2010/0249589 | A1 | 9/2010 | Lysyansky et al. | |
| 2011/0319761 | A1 | 12/2011 | Abe et al. | |
| 2012/0165674 | A1* | 6/2012 | Abe | A61B 8/0883 600/443 |
| 2012/0253206 | A1* | 10/2012 | Fukuda | A61B 5/0452 600/483 |
| 2015/0018684 | A1* | 1/2015 | Abe | A61B 8/14 600/443 |
| 2015/0038846 | A1 | 2/2015 | Abe et al. | |
| 2015/0342571 | A1 | 12/2015 | Ohuchi et al. | |
| 2017/0252011 | A1* | 9/2017 | Abe | A61B 8/5223 |

FOREIGN PATENT DOCUMENTS

| | | |
|---|---|---|
| JP | 2012-55483 | 3/2012 |
| JP | 2012-157608 A | 8/2012 |
| JP | 2012-187383 | 10/2012 |
| JP | 2013-226400 | 11/2013 |
| JP | 2014-171556 A | 9/2014 |

OTHER PUBLICATIONS

Japanese Office Action dated Feb. 24, 2021 Japanese Patent Application No. 2016-245637, 4 pages.

* cited by examiner

INITIAL TIME
PHASE

ULTRASONIC DIAGNOSTIC APPARATUS AND IMAGE PROCESSING METHOD

CROSS-REFERENCE TO RELATED APPLICATIONS

This application is based upon and claims the benefit of priority from Japanese Patent Application No. 2016-041100, filed on Mar. 3, 2016; and Japanese Patent Application No. 2016-245637, filed on Dec. 19, 2016, the entire contents of all of which are incorporated herein by reference.

FIELD

Embodiments described herein relate generally to an ultrasonic diagnostic apparatus and an image processing method.

BACKGROUND

Conventionally, a technique referred to as speckle tracking echocardiography has been well-known, with which a cardiac wall motion is tracked in image data in order to quantitatively evaluate a wall motion of the heart of a subject. With respect to the speckle tracking, a two-dimensional speckle tracking (2DT) which is applied on two-dimensional moving image data and a three-dimensional speckle tracking (3DT) which is applied on three-dimensional moving image data have been known.

In 2DT, for example, from an analysis result of 2DT, an index value that does not depend on a time is defined. Based on this, 2DT analysis results based on a plurality of cross sections related to the same subject, which have been collected in different times of day, are synthesized. Pieces of image information of the cross sections which have been collected in different times of day include heart rate variation and differences in scan conditions such as a frame rate. Because of this, the settings and the conditions in the time direction are not uniform among the cross sections. To deal with this, for example, a peak systolic strain (PSS) value is defined, with which the strain value in each cross section is a peak during a period from the end-diastole to the end-systole. With this, the analysis results from the cross sections are synthesized without consideration for the differences in the time of day. As an example, values among cross sections are spatially interpolated using the PSS values for the cross sections whereby polar map display of the PSS values is performed.

Furthermore, a technique has been proposed that uses 2DT of a plurality of cross sections to present volume information of the left ventricle by the bi-plane disk-summation method (modified-Simpson method). In this case, after heart rate variation and differences in frame rates in collecting the pieces of image information of each of the cross sections are corrected, volume information in various cardiac time phases is obtained.

Furthermore, in 3DT, a technique has been proposed that uses three-dimensional strain value changes of the heart as function information to present three-dimensional display, polar map display, and moving image data of an MPR cross section. In this case, a technique of activation imaging (AI) is performed with which at a point where the strain value for one position has once arrived at a predetermined threshold, myocardial contraction is regraded as activated, and a pixel value (luminance value) in accordance with the arrival time value of contraction to that position is retained and output, for example.

DETAILED DESCRIPTION

An ultrasonic diagnostic apparatus according to an embodiment includes a processing circuitry. With respect to pieces of image data of a plurality of cross sections passing through the heart of a subject that have been collected by ultrasonically scanning each of the cross sections for a period of at least one heart beat, the processing circuitry performs tracking processing including two-dimensional pattern matching to generate pieces of analysis information in each of which a cardiac wall motion of the heart in each section is analyzed. The processing circuitry matches time phases of the pieces of analysis information of the cross sections and maps the pieces of analysis information of the cross sections with the matched time phases on a predetermined polar coordinate system to generate a polar coordinate display image. The processing circuitry causes display of the polar coordinate display image.

An ultrasonic diagnostic apparatus and an image processing method according to an embodiment will be described below with reference to the drawings.

First Embodiment

Figure 1:
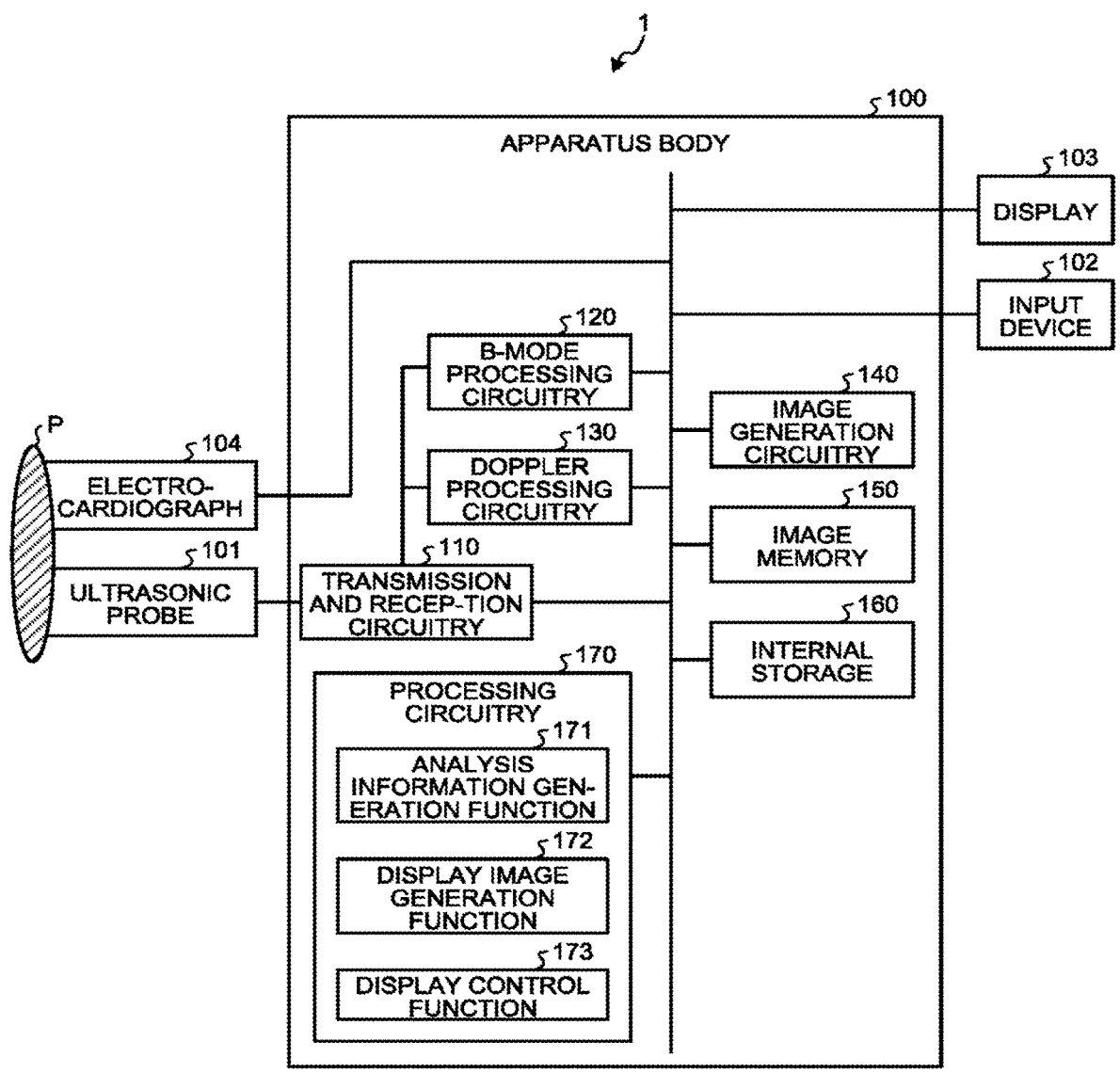
FIG. 1 is a block diagram illustrating an exemplary configuration of an ultrasonic diagnostic apparatus according to a first embodiment.

Firstly, the configuration of an ultrasonic diagnostic apparatus according to a first embodiment will be described. FIG. 1 is a block diagram illustrating an exemplary configuration of an ultrasonic diagnostic apparatus 1 according to a first embodiment. As illustrated in FIG. 1, the ultrasonic diagnostic apparatus 1 according to the first embodiment includes an apparatus body 100, an ultrasonic probe 101, an input device 102, a display 103, and an electrocardiograph 104. The ultrasonic probe 101, the input device 102, the display 103, and the electrocardiograph 104 are communicably connected to the apparatus body 100.

The ultrasonic probe 101 includes a plurality of piezoelectric transducer elements. These piezoelectric transducer elements generate ultrasonic waves based on drive signals supplied from a transmission and reception circuitry 110 included in the apparatus body 100. Furthermore, the ultrasonic probe 101 receives a reflected wave from the subject P and converts the received reflected wave to an electrical signal. The ultrasonic probe 101 also includes a matching layer provided on a piezoelectric transducer element and a backing material that prevents propagation of ultrasonic waves from the piezoelectric transducer elements to the rear thereof, for example. It should be noted that the ultrasonic probe 101 is detachably connected to the apparatus body 100.

Once ultrasonic waves have been transmitted from the ultrasonic probe 101 to the subject P, the transmitted ultrasonic waves are reflected sequentially on discontinuous surfaces of acoustic impedance in the body tissues of the subject P and received by the piezoelectric transducer elements included in the ultrasonic probe 101 as reflected wave signals. The amplitude of the received wave signals depends on an acoustic impedance difference on the discontinuous surfaces on which the ultrasonic waves are reflected. It should be noted that the reflected wave signals, in a case where transmitted ultrasonic pulses are reflected on the surface of a blood flow that is moving, a cardiac wall, or the like, receive frequency transition due to the Doppler effect depending on a velocity component with respect to the transmission direction of the ultrasonic waves of the moving body.

In the first embodiment, the ultrasonic probe 101 that two-dimensionally scans the subject P with ultrasonic waves is used. For example, the ultrasonic probe 101 is a 1D array probe on which a plurality of piezoelectric transducer elements are arranged in a line. The 1D array probe is a sector-type ultrasonic probe, a linear-type ultrasonic probe, and a convex-type ultrasonic probe, for example. However, in the first embodiment, the ultrasonic probe 101 may be, for example, a mechanical 4D probe or a 2D array probe that can two-dimensionally scan as well as three-dimensionally scan the subject P with ultrasonic waves. The mechanical 4D probe can perform two-dimensional scan using a plurality of piezoelectric transducer elements arranged in a line as well as three-dimensional scan by oscillating the piezoelectric transducer elements arranged in a line at a predetermined angle (oscillation angle). Furthermore, the 2D array probe can perform three-dimensional scan using a plurality of piezoelectric transducer elements arranged in a matrix form as well as two-dimensional scan with converged ultrasonic waves transmitted and received. It should be noted that the 2D array probe also can simultaneously perform two-dimensional scan of a plurality of cross sections.

The input device 102 includes a mouse, a keyboard, a button, a panel switch, a touch command screen, a foot switch, a trackball, a joystick, and the like, receives various setting requests from an operator of the ultrasonic diagnostic apparatus 1, and transfers the received various setting requests to the apparatus body 100.

The display 103 displays a graphical user interface (GUI) for the operator of the ultrasonic diagnostic apparatus 1 to use the input device 102 to input the various setting requests and displays ultrasonic image data generated in the apparatus body 100, for example. Furthermore, the display 103 displays various messages to notify a condition of processing of the apparatus body 100 to the operator. The display 103 also includes a speaker for outputting a sound. For example, the speaker of the display 103 outputs a predetermined sound such as a beep sound to notify a condition of processing of the apparatus body 100 to the operator.

The electrocardiograph 104 acquires an electrocardiogram (ECG) of the subject P as a biomedical signal of the subject P who is two-dimensionally scanned. The electrocardiograph 104 transmits the acquired electrocardiogram to the apparatus body 100. It should be noted that in the present embodiment, a case is described where the electrocardiograph 104 is used as a means of acquiring information related to the cardiac time phase of the heart of the subject. However, the embodiment is not limited thereto. For example, the ultrasonic diagnostic apparatus 1 may acquire a time at which the intramyocardial volume calculated by two-dimensional speckle tracking (2DT) described later is the minimum as an end systolic time (ESt) to acquire information related to the cardiac time phase of the heart of the subject. Furthermore, the ultrasonic diagnostic apparatus 1 may acquire a time of the II sound (second sound) in a phonocardiogram or an aortic valve close (AVC) time obtained by measuring the ejection blood flow of the heart using the spectral Doppler method to acquire information related to the cardiac time phase of the heart of the subject.

The apparatus body 100 is an apparatus that generates ultrasonic image data based on the reflected wave signals received by the ultrasonic probe 101. The apparatus body 100 illustrated in FIG. 1 is an apparatus that can generate two-dimensional ultrasonic image data based on two-dimensional reflected wave signals received by the ultrasonic probe 101.

The apparatus body 100 includes a transmission and reception circuitry 110, a B-mode processing circuitry 120, a Doppler processing circuitry 130, an image generation circuitry 140, an image memory 150, an internal storage 160, and a processing circuitry 170, as illustrated in FIG. 1.

The transmission and reception circuitry 110 includes a pulse generator, a transmission delay unit, a pulsar, and the like, and supplies a drive signal to the ultrasonic probe 101. The pulse generator repeatedly generates a rate pulse for forming transmission ultrasonic waves at a predetermined rate frequency. Furthermore, the transmission delay unit converges the ultrasonic waves generated from the ultrasonic probe 101 in a beam form and gives a delay time for each piezoelectric transducer element necessary for deciding the transmission directivity to each rate pulse generated by the pulse generator. Furthermore, the pulsar applies a drive signal (drive pulse) to the ultrasonic probe 101 at a timing based on the rate pulse. More specifically, the transmission delay unit changes the delay time given to each rate pulse, thereby optionally adjusting the transmission direction of the ultrasonic waves transmitted from the piezoelectric transducer element surface.

The transmission and reception circuitry 110 includes a function capable of instantaneously changing the transmission frequency, transmission drive voltage, and the like to perform a predetermined scan sequence based on an instruction of the processing circuitry 170 described later. Especially, change of the transmission drive voltage is implemented by a linear amplifier-type transmitting circuit that can instantaneously switch the value thereof or a mechanism that electrically switches among a plurality of power supply units.

Furthermore, the transmission and reception circuitry 110 includes a preamplifier, an analog/digital (A/D) converter, a reception delay unit, an adder, and the like, and generates reflected wave data by performing various types of processing with respect to the reflected wave signals received by the ultrasonic probe 101. The preamplifier amplifies the reflected wave signals for each channel. The A/D converter converts the amplified reflected wave signals. The reception delay unit gives a delay time necessary for deciding the reception directivity. The adder generates reflected wave data by performing addition processing of the reflected wave signals processed by the reception delay unit. By the addition processing performed by the adder, a reflection component from the direction in accordance with the reception directivity of the reflected wave signals is emphasized and an overall beam of ultrasonic transmission and reception is formed by the reception directivity and the transmission directivity.

The transmission and reception circuitry 110 causes the ultrasonic probe 101 to transmit two-dimensional ultrasonic beams when the subject P is two-dimensionally scanned. The transmission and reception circuitry 110 then generates two-dimensional reflected wave data from the two-dimensional reflected wave signals received by the ultrasonic probe 101.

At this point, the mode of the output signal from the transmission and reception circuitry 110 may be selected from various types. For example, the output signal may be a signal including phase information, which is referred to as a radio frequency (RF) signal, or a signal including amplitude information after envelope detection processing is applied.

The B-mode processing circuitry 120 receives reflected wave data from the transmission and reception circuitry 110 and performs logarithmic amplification, envelope detection processing, and the like to generate data in which the signal intensity is represented by the brightness of the luminance (B mode data).

The Doppler processing circuitry 130 performs frequency analysis on velocity information from the reflected wave data received from the transmission and reception circuitry 110, extracts blood flow components, tissue components, and contrast agent echo components due to the Doppler effect, and generates data in which moving body information such as velocity, variance, and power are extracted at multiple points (Doppler data).

The B-mode processing circuitry 120 and the Doppler processing circuitry 130 illustrated in FIG. 1 can process both two dimensional reflected wave data and three-dimensional reflected wave data. More specifically, the B-mode processing circuitry 120 generates two-dimensional B-mode data from two-dimensional reflected wave data and generates three-dimensional B-mode data from three-dimensional reflected wave data. Furthermore, the Doppler processing circuitry 130 generates two-dimensional Doppler data from two-dimensional reflected wave data and generates three-dimensional Doppler data from three-dimensional reflected wave data.

The image generation circuitry 140 generates ultrasonic image data from data generated by the B-mode processing circuitry 120 and the Doppler processing circuitry 130. More specifically, the image generation circuitry 140 generates two-dimensional B-mode image data in which the intensity of the reflected wave is represented by the luminance from the two-dimensional B-mode data generated by the B-mode processing circuitry 120. Furthermore, the image generation circuitry 140 generates two-dimensional Doppler image data representing moving body information from the two-dimensional Doppler data generated by the Doppler processing circuitry 130. The two-dimensional Doppler data is for a velocity image, a variance image, a power image, or an image combining these. Furthermore, the image generation circuitry 140 also can generate M-mode image data from time-series data of the B-mode data on one scanning line generated by the B-mode processing circuitry 120. The image generation circuitry 140 also can generate a Doppler waveform that plots pieces of velocity information of blood flows and tissues along time series from the Doppler data generated by the Doppler processing circuitry 130.

At this point, the image generation circuitry 140 generally converts (scan-converts) a scanning line signal string of ultrasonic scan into a scanning line signal string in a video format, which is typified by television, for example, to generate ultrasonic image data for display. More specifically, the image generation circuitry 140 performs coordinate conversion in accordance with the scanning mode of ultrasonic waves used by the ultrasonic probe 101, thereby generating the ultrasonic image data for display. Furthermore, besides the scan conversion, as various types of image processing, the image generation circuitry 140 performs image processing of regenerating an average value image of luminance using a plurality of image frames after the scan conversion (smoothing processing) and image processing using a differential filter in an image (edge emphasis processing), for example. Furthermore, the image generation circuitry 140 synthesizes character information of various parameters, scales, body marks, and the like with the ultrasonic image data.

More specifically, each of the B-mode data and the Doppler data is ultrasonic image data before scan conversion processing and the data generated by the image generation circuitry 140 is the ultrasonic image data for display after scan conversion processing. It should be noted that each of the B-mode data and the Doppler data is also referred to as raw data. The image generation circuitry 140 generates "two-dimensional B-mode image data and two-dimensional Doppler image data" being two-dimensional ultrasonic image data for display from "two-dimensional B-mode data and two-dimensional Doppler data" being two-dimensional ultrasonic image data before scan conversion.

The image memory 150 is a memory that stores therein the image data for display generated by the image generation circuitry 140. Furthermore, the image memory 150 also can store therein the data generated by the B-mode processing circuitry 120 or the data generated by the Doppler processing circuitry 130. Each of the B-mode data and the Doppler data stored in the image memory 150 can be called by the operator after diagnosis, for example, and becomes the ultrasonic image data for display via the image generation circuitry 140.

The image generation circuitry 140 stores the ultrasonic image data and the time for the ultrasonic scan performed to generate that ultrasonic image data in the image memory 150 in association with electrocardiographic waveforms transmitted from the electrocardiograph 104. The processing circuitry 170 described later can acquire the cardiac time phase at the time of the ultrasonic scan performed to generate the ultrasonic image data by referring to the data stored in the image memory 150.

The internal storage 160 stores therein a control program for performing ultrasonic transmission and reception, image processing, and display processing, diagnostic information (a patient ID and a doctor's observation, for example), and various types of data such as a diagnostic protocol and various body marks. Furthermore, the internal storage 160 is used for storage of image data stored in the image memory 150 as necessary, for example. Furthermore, data stored in the internal storage 160 can be transferred to an external device via an interface which is not illustrated. It should be noted that the external device is, for example, a personal computer (PC) used by a doctor who performs image diagnosis, a storage medium such as a CD and a DVD, and a printer.

The processing circuitry 170 controls the overall processing of the ultrasonic diagnostic apparatus 1. Specifically, the processing circuitry 170 controls processing of the transmission and reception circuitry 110, the B-mode processing circuitry 120, the Doppler processing circuitry 130, and the image generation circuitry 140 based on the various setting request input by the operator via the input device 102 and the various control programs and various types of data read from the internal storage 160. Furthermore, the processing circuitry 170 controls the ultrasonic image data for display stored in the image memory 150 and the internal storage 160 to be displayed on the display 103.

Furthermore, the processing circuitry 170 performs an analysis information generation function 171, a display image generation function 172, and a display control function 173. It should be noted that the details of processing of the analysis information generation function 171, the display image generation function 172, and the display control function 173 that the processing circuitry 170 performs will be described later.

At this point, for example, each of various processing functions performed by the analysis information generation function 171, the display image generation function 172, and the display control function 173, which are components of the processing circuitry 170 illustrated in FIG. 1, is stored in the internal storage 160 in a form of a computer-executable program. The processing circuitry 170 is a processor that reads each of the programs from the internal storage 160 and executes the read programs, thereby implementing the function corresponding to that program. In other words, the processing circuitry 170 in a state in which each program is read out has each of the functions illustrated inside the processing circuitry 170 in FIG. 1.

In the present embodiment, description is made based on the assumption that various processing functions described below are implemented in a single processing circuitry 170. However, a processing circuit may be structured by combining a plurality of independent processors, so that each processor executes a computer program to implement a function.

The term "processor" used in the description above represents a central processing unit (CPU), a graphics processing unit (GPU), or a circuit such as an application specific integrated circuit (ASIC) and a programmable logic device (a simple programmable logic device (SPLD), a complex programmable logic device (CPLD), and a field programmable gate array (FPGA), for example). The processor reads out a computer program stored in the internal storage 160 and executes the read computer program to implement a function. It should be noted that instead of storing the computer program in the internal storage 160, the program may be configured to be directly embedded in the circuit of the processor. In this case, the processor reads out a computer program embedded in the circuit and executes the read computer program to implement a function. It should be noted that each processor in the present embodiment is not limited to one structured as a single processor, and a plurality of independent processors may be structured as one processor to implement the functions thereof. Furthermore, a plurality of components in each drawing may be integrated into one processor to implement the functions thereof.

The overall configuration of the ultrasonic diagnostic apparatus 1 according to the first embodiment has been described above. With this configuration, the ultrasonic diagnostic apparatus 1 according to the first embodiment can display a polar coordinate display image (hereinafter, also referred to as a polar map) in a manner matching the time phases of pieces of image data of a plurality of cross sections that have been separately collected. For example, the ultrasonic diagnostic apparatus 1 performs ultrasonic scan of each of a plurality of cross sections passing through the heart of the subject P for a period of at least one heart beat, thereby collecting pieces of ultrasonic image data of the cross sections separately. The ultrasonic diagnostic apparatus 1 then matches the time phases of the pieces of ultrasonic image data for the cross sections separately collected, thereby enabling display of information related to the time-series change of the cardiac wall motion on a polar map.

Figure 2:
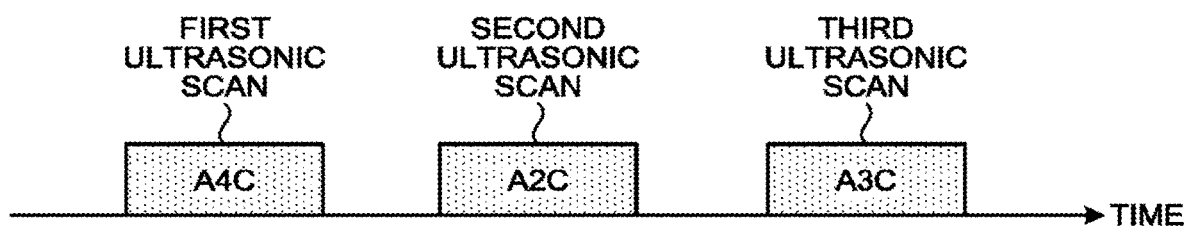
FIG. 2 is a diagram for explaining ultrasonic scan of a plurality of cross sections according to the first embodiment.

FIG. 2 is a diagram for explaining ultrasonic scan of a plurality of cross sections according to the first embodiment. In FIG. 2, the horizontal axis corresponds to a time. As illustrated in FIG. 2, for example, the operator uses a sector-type ultrasonic probe 101 to collect pieces of ultrasonic image data of three cross sections separately by an apical approach. To be specific, firstly, to collect apical four chamber (A4C) views being one of long-axis views of the heart along time series, the operator performs ultrasonic scan of the A4C plane for a period of one heart beat or longer (first ultrasonic scan). With this operation, the image generation circuitry 140 generates a plurality of pieces of two-dimensional B-mode image data (moving image data) of the A4C plane along time series for a period of one heart beat or longer and stores the generated pieces of two-dimensional B-mode image data in the image memory 150. Furthermore, to collect apical two chamber (A2C) views being one of long-axis views of the heart along time series, the operator performs ultrasonic scan of the A2C plane for a period of one heart beat or longer (second ultrasonic scan). With this operation, the image generation circuitry 140 generates a plurality of pieces of two-dimensional B-mode image data of the A2C plane along time series for a period of one heart beat or longer and stores the generated pieces of two-dimensional B-mode image data in the image memory 150. Furthermore, to collect apical three chamber (A3C) views being one of long-axis views of the heart along time series, the operator performs ultrasonic scan of the A3C plane for a period of one heart beat or longer (third ultrasonic scan). With this operation, the image generation circuitry 140 generates a plurality of pieces of two-dimensional B-mode image data of the A3C plane along time series for a period of one heart beat or longer and stores the generated pieces of two-dimensional B-mode image data in the image memory 150. It should be noted that the A3C view is also referred to as an apical long axis view (A-LAX).

As described above, the ultrasonic diagnostic apparatus 1 according to the first embodiment performs ultrasonic scan of a plurality of cross sections sequentially with respect to the same subject in different times of day, thereby collecting a plurality of pieces of ultrasonic image data (a set of ultrasonic image data) along time series for each of the cross sections separately.

At this point, as illustrated in FIG. 2, in a case where pieces of ultrasonic image data of a plurality of cross sections are separately collected in different times of day, the time phases included in the collected pieces of ultrasonic image data of each of the cross sections change due to the heart beat fluctuation of the subject. For example, the length of one heart beat in the time of day in which the first ultrasonic scan is performed and the length of one heart beat in the time of day in which the second ultrasonic scan change.

Furthermore, in a case where the pieces of ultrasonic image data are separately collected, the ultrasonic scan of each cross section is not necessarily performed with the same frame rate. For example, in a case where the visual field depth of a collected cross section is deepened or the scanning field angle is widened, the frame rate needs to be lowered in some cases. More specifically, in a case where the pieces of ultrasonic image data are separately collected, the frame rate of each cross section may be changed, and the time intervals in the set of ultrasonic image data of each cross section thus vary in accordance with the change of the frame rate.

To solve this problem, the ultrasonic diagnostic apparatus 1 according to the first embodiment performs each of the functions of the processing circuitry 170 described below to display a polar map in a manner matching the time phases of the pieces of image data of a plurality of cross sections that have been separately collected.

With respect to the pieces of image data of a plurality of cross sections passing through the heart of the subject that have been collected by ultrasonically scanning each of the cross sections for a period of at least one heart beat, the analysis information generation function 171 performs tracking processing including two-dimensional pattern matching, thereby generating analysis information in which the cardiac wall motion of the subject in each cross section is analyzed. For example, the analysis information generation function 171 generates analysis information of each cross section from the pieces of image data collected in different times of day. It should be noted that the analysis information generation function 171 is an example of an analysis information generation unit.

Firstly, the analysis information generation function 171 acquires a plurality of sets of two-dimensional ultrasonic image data collected by ultrasonically scanning each of predetermined cross sections for a period of at least one heart beat. For example, the analysis information generation function 171 acquires a plurality of sets of two-dimensional ultrasonic image data of the A4C plane along times series for one heart beat interval (sets of A4C images). Furthermore, the analysis information generation function 171 acquires a plurality of sets of two-dimensional ultrasonic image data of the A2C plane along times series for one heart beat interval (sets of A2C images). Furthermore, the analysis information generation function 171 acquires a plurality of sets of two-dimensional ultrasonic image data of the A3C plane along times series for one heart beat interval (sets of A3C images). At this point, the analysis information generation function 171 detects a time phase being a feature wave (an R-wave or a P-wave, for example) from electrocardiographic waveforms acquired by the electrocardiograph 104 and acquires the detected time phase in association with the time of ultrasonic scan for the ultrasonic image data sets of each cross section.

The analysis information generation function 171 then performs tracking processing including two-dimensional pattern matching across a predetermined interval to acquire time series data of the positions of the interior, exterior, and contour of a cavity of a predetermined region included in each of the sets of two-dimensional ultrasonic image data. More specifically, the analysis information generation function 171 performs 2D speckle tracking (2DT) processing with respect to two-dimensional moving image data. The speckle tracking method is a method of estimating an accurate motion by performing an optical flow method and various types of spatiotemporal interpolation processing, for example, in combination with pattern matching.

At this point, the analysis information generation function 171 acquires the contour position of at least one of the ventricles and atria of the heart as a predetermined region. More specifically, a region to be processed with the 2DT processing is one or more regions selected by the operator from the interior of the right atrium, the exterior of the right atrium, the interior of the right ventricle, the exterior of the right ventricle, the interior of the left atrium, the exterior of the left atrium, the interior of the left ventricle, and the exterior of the left ventricle. In the description below, a case will be described where as a region to be processed with the 2DT processing, the interior of the left ventricle and the exterior of the left ventricle are selected.

For example, the input device 102 receives a setting request for a tracking point from the operator. The processing circuitry 170 to which the setting request for the tracking point is transferred reads out pieces of two-dimensional ultrasonic image data in the initial time phase from the image memory 150 and causes the display 103 to display images therefrom. Specifically, the processing circuitry 170 uses the first frame (starting frame) of pieces of moving image data as the first time phase to read out an A4C image, an A2C image, and an A3C image in the first frame and cause the display 103 to display images therefrom.

Figure 3:
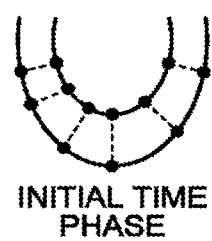
FIG. 3 is a diagram for explaining processing of an analysis information generation function according to the first embodiment.

FIG. 3 is a diagram for explaining processing of the analysis information generation function 171 according to the first embodiment. In FIG. 3, a tracking point set to the piece of ultrasonic image data in the first frame out of the sets of A4C images.

As illustrated in FIG. 3, the operator sets a tracking point for performing 2DT by referring the piece of two-dimensional ultrasonic image data of the A4C plane in the initial time phase. For example, the operator traces the endocardium of the left ventricle and the epicardium of the left ventricle using a mouse of the input device 102 in the piece of two-dimensional ultrasonic image data in the initial time phase. The analysis information generation function 171 reconstructs two two-dimensional boundary planes from the traced endocardium and epicardium as two contours in the initial time phase (initial contours). The analysis information generation function 171 then sets a plurality of tracking points in each of the contour of the endocardium and the contour of the epicardium in the initial time phase as illustrated in FIG. 3. The analysis information generation function 171 sets template data with respect to each of the tracking points set in the frame of the initial time phase. The template data is formed of a plurality of pixels centered on the tracking point.

The analysis information generation function 171 then searches for a region that matches the best with the speckle pattern of the template data between two frames, thereby tracking to what position the template data is moved in the next frame. With this tracking processing, the analysis information generation function 171 acquires the position of each tracking point in the sets of two-dimensional ultrasonic image data other than the piece of two-dimensional ultrasonic image data in the initial time phase.

With this, the analysis information generation function 171 acquires time series data of the contour position including the endocardium and the epicardium of the left ventricle with respect to the sets of ultrasonic image data for each of a plurality of cross sections. For example, the analysis information generation function 171 acquires time series data of the contour position of the left ventricle included in A4C images, time series data of the contour position of the left ventricle included in A2C images, and time series data of the contour position of the left ventricle included in A3C images.

The analysis information generation function 171 then generates a strain value that represents a strain of the cardiac wall of the heart of the subject P from the acquired time series data of the contour position of the left ventricle in the sets of ultrasonic image data of each cross section. For example, the analysis information generation function 171 obtains time series change of the length of a tracking point pair between two points in a preset direction for strain measurement with respect to each of the cross sections and generates this as a strain value. Specifically, the analysis information generation function 171 obtains time series change of the length of a tracking point pair between two points in a preset direction with respect to the A4C images and generates this as a strain value of the A4C images. Furthermore, the analysis information generation function 171 obtains time series change of the length of a tracking point pair between two points in a preset direction with respect to the A2C images and generates this as a strain value of the A2C images. Furthermore, the analysis information generation function 171 obtains time series change of the length of a tracking point pair between two points in a preset direction with respect to the A3C images and generates this as a strain value of the A3C images. At this point, as the preset direction, two types, which are the tangential direction of the contour and the wall thickness direction between the endocardium and the epicardium are preferable. It should be noted that the strain value in each cross section preferably represents time change based on one time phase (initial time phase or the time phase of an R wave) and is output as a time curve.

In the example described above, a case has been described where a strain value is generated as analysis information. However, the embodiment is not limited thereto. For example, the analysis information generation function 171 may generate an arrival time value with which a strain value arrives at a threshold as analysis information. Furthermore, the analysis information generation function 171 may use not only a strain value or an arrival time value but the contour position of a tracked endocardium surface to generate information on the volume, based on a modified Simpson method, a disk summation method, an area length method, or the like.

Furthermore, the setting of the initial contour is not limited to one that is manually performed by the operator as described above. For example, the setting of the initial contour may be automatically performed as described below. For example, the analysis information generation function 171 estimates the position of the initial contour from the position of the valve annulus and the position of the apex specified by the operator in the piece of image data of the initial time phase. Alternatively, for example, the analysis information generation function 171 estimates the position of the initial contour from the piece of image data of the initial time phase without receiving information from the operator. The automatic estimation methods described above use a boundary estimation technique with which the luminance information of an image is used and a boundary estimation technique with which a shape database registered in advance as "shape information of the heart" and the features of the image are compared and collated with a discriminator.

The display image generation function 172 matches the time phases of the pieces of analysis information of the cross sections and maps the pieces of analysis information of the cross sections with the matched time phases on a predetermined polar coordinate system to generate a polar coordinate display image (polar map). For example, the display image generation function 172 matches the time phases of the pieces of analysis information of the cross sections in different times of day with a predetermined cardiac time phase as a reference. It should be noted that the display image generation function 172 is an example of a display image generation unit.

Figure 4:
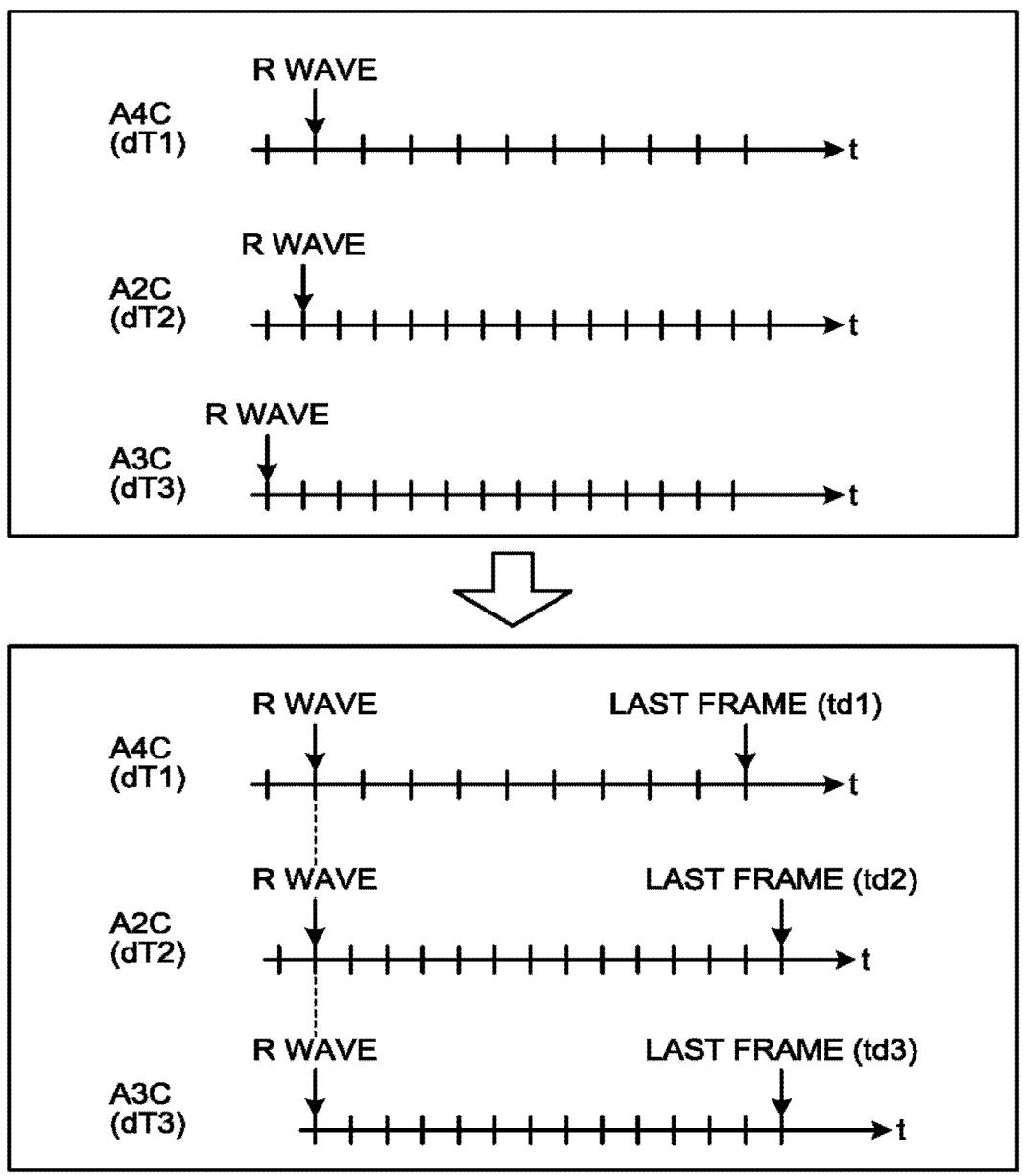
FIG. 4 is a diagram for explaining processing of a display image generation function according to the first embodiment.

FIG. 4 is a diagram for explaining processing of the display image generation function 172 according to the first embodiment. FIG. 4 exemplifies processing of the display image generation function 172 in a case where the time phases of the A4C plane, the A2C plane, and the A3C plane are matched. In FIG. 4, the horizontal axis corresponds to a time t (frame in the moving image data). Furthermore, in FIG. 4, the exemplification is made on the assumption that the frame interval of the moving image data of the A4C plane is "dT1", the frame interval of the moving image data of the A2C plane is "dT2", and the frame interval of the moving image data of the A3C plane is "dT3". It should be noted that in this example, dT3<dT2<dT1.

As illustrated in FIG. 4, the display image generation function 172 matches the starting point of the time series data of the A4C images, the starting point of the time series data of the A2C images, and the starting point of the time series data of the A3C images in accordance with the R-wave time phase, for example (see the lower figure in FIG. 4). The display image generation function 172 then calculates an arrival time with which the strain value in each cross section arrives at a predetermined variable threshold (ex. 0 to 100 [%] of each peak strain value) with the matched starting points (R-wave time phase) as a reference time phase. At this point, the arrival time value is a value being an index of a technique (activation imaging (AI)), with which at a point where the strain value for one position (sample position) has once arrived at the predetermined threshold, myocardial contraction is regraded as activated and a pixel value (luminance value) in accordance with the arrival time value is displayed. For this reason, an arrival time value is also referred to as an "AI value". To cite an example, the AI value is defined as a time [msec] at which a local strain value in the longitudinal direction (longitudinal strain (LS)) arrives at the level of 30% as typical predetermined variable threshold with respect to a peak value in one cardiac cycle of each location. It should be noted that the reference time phase represents the time phase being the reference (time zero) when calculating an arrival time value.

For example, the display image generation function 172 calculates an arrival time value $AI1(t)$ at which the strain value at each point forming the tracked contour of an A4C image arrives at the level of 30% with respect to the peak value in one cardiac cycle of the point with the R-wave time phase as the reference time phase. Furthermore, the display image generation function 172 calculates an arrival time value AI2(t) at which the strain value at each point forming the contour of an A2C image arrives at the level of 30% with respect to the peak value in one cardiac cycle of the point with the R-wave time phase as the reference time phase. Furthermore, the display image generation function 172 calculates an arrival time value AI3(t) at which the strain value at each point forming the contour of an A3C image arrives at the level of 30% with respect to the peak value in one cardiac cycle of the point with the R-wave time phase as the reference time phase. It should be noted that t corresponds to a time in the moving image data of each cross section (frame).

The display image generation function 172 then selects a predetermined time phase td as the time t. At this point, the time td is preset in advance so that the last frame is selected. As a result, the display image generation function 172 selects a last frame td1 of an A4C image, a last frame td2 of an A2C image, and a last frame td3 of an A3C image. With this, the display image generation function 172 calculates an arrival time value AI1 of an A4C image (td1), an arrival time value AI2 of an A2C image (td2), and an arrival time value AI3 of an A3C image (td3). The display image generation function 172 then uses the calculated arrival time values AI1 (td1), AI2 (td2), and AI3 (td3) of each cross section to generate a polar map.

Figure 5:
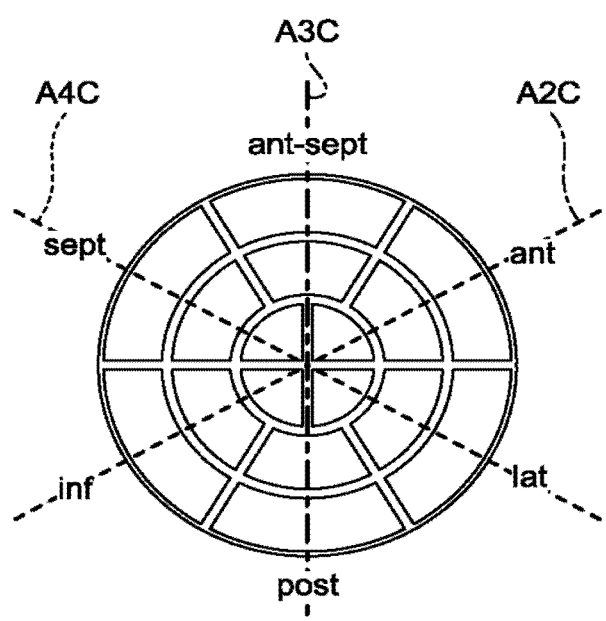
FIG. 5 is a diagram for explaining processing of the display image generation function according to the first embodiment.

FIG. 5 is a diagram for explaining processing of the display image generation function 172 according to the first embodiment. FIG. 5 exemplifies a case where the arrival time values AI1 (td1), AI2 (td2), and AI3 (td3) of three cross sections of the A4C plane, the A2C plane, and the A3C plane are synthesized to generate a polar map. At this point, a polar map indicates a display mode in which cardiac function information of each position (pixel) set on the surface of the left ventricle is displayed in a manner developed on a two-dimensional plane with the apex serving as a pole and is also referred to as a bull's eye plot. For example, as a general fractionation model, a display mode is cited in which fractionation into 16 to 17 segments is performed in the directions of the anterior wall (ant), the anteroseptal (ant-sept), the septum (sept), the inferior wall (inf), the posterior wall (post), and the lateral wall (lat).

At this point, each point on the A4C image corresponds to a point on a straight line passing through the septum (sept) and the lateral wall (lat) on the polar map. Furthermore, each point on the A2C image corresponds to a point on a straight line passing through the anterior wall (ant) and the inferior wall (inf) on the polar map. Furthermore, each point on the A3C image corresponds to a point on a straight line passing through the anteroseptal (ant-sept) and the posterior wall (post) on the polar map. The display image generation function 172 then uses a piece of cardiac function information for each of a plurality of cross sections to perform spatial interpolation processing (in the circumferential direction of the map) on a point on a pair of positions in the corresponding longitudinal direction (a corresponded radius on the map), thereby generating a polar map (synthesized polar map).

As illustrated in FIG. 5, the display image generation function 172 calculates the arrival time value of each point between the A4C plane and the A2C plane by performing interpolation processing in the circumferential direction using the arrival time value AI1 of the A4C image (td1) and the arrival time value AI2 of the A2C image (td2). Furthermore, the display image generation function 172 calculates the arrival time value of each point between the A4C plane and the A3C plane by performing interpolation processing in the circumferential direction using the arrival time value AI1 of the A4C image (td1) and the arrival time value AI3 of the A3C image (td3). Furthermore, the display image generation function 172 calculates the arrival time value of each point between the A2C plane and the A3C plane by performing interpolation processing in the circumferential direction using the arrival time value AI2 of the A2C image (td2) and the arrival time value AI3 of the A3C image (td3). The display image generation function 172 then allocates a pixel value corresponding to the calculated arrival time value of each point to generate a synthesized polar map.

As described above, the display image generation function 172 uses the arrival time value of each of the cross sections to generate a polar map. It should be noted that in the description above, a case has been described where the last frame is selected as the time phase td in the time domain for detecting an arrival time value. However, the embodiment is not limited thereto, and an optional time phase td may be selected. However, to calculate the arrival time value of each point, as the time phase td, the last frame corresponding to the time after one cardiac cycle has elapsed is preferably selected.

The display control function 173 displays a polar coordinate display image. For example, the display control function 173 causes the display 103 to display a polar map generated by the display image generation function 172. It should be noted that the display control function 173 is an example of a display control unit.

Figure 6:
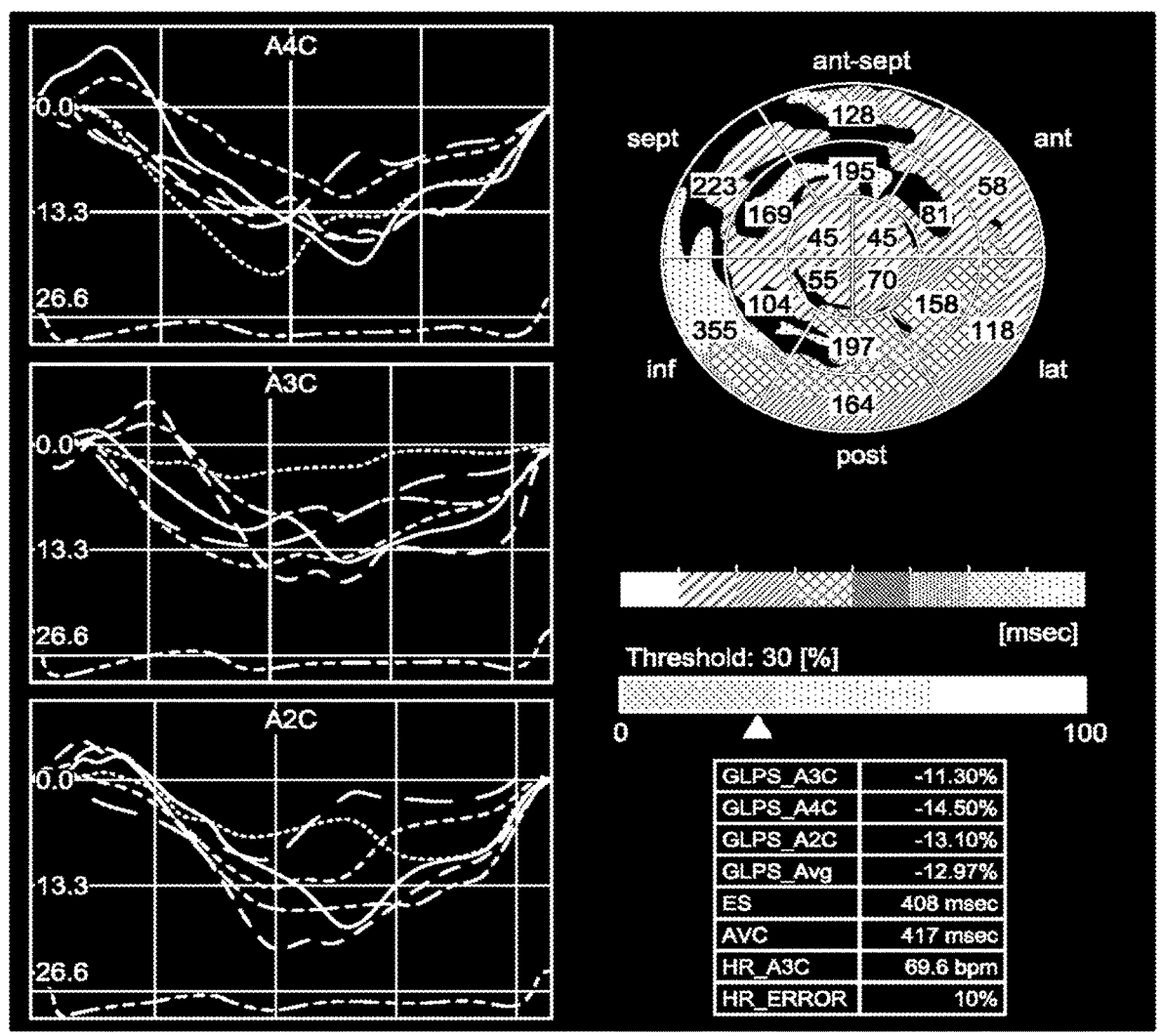
FIG. 6 is a diagram for explaining processing of a display control function according to the first embodiment.

FIG. 6 is a diagram for explaining processing of the display control function 173 according to the first embodiment. FIG. 6 exemplifies a display screen displayed on the display 103 by the processing of the display control function 173.

As illustrated in FIG. 6, the display control function 173 causes the display 103 to display the polar map generated by the display image generation function 172 as a still image (see the upper right figure in FIG. 6). Furthermore, the display control function 173 causes the average value of the arrival time value [msec] in each segment to be displayed on the segment of the polar map.

Furthermore, the display control function 173 displays an index value of the heart beat fluctuation among each of the cross sections. For example, the display control function 173 calculates a difference in the heart beats among each of the cross sections and displays the calculated difference on the display 103. More specifically, the display control function 173 displays an index value "HR_ERROR" of fluctuation of one cardiac cycle among the cross sections.

For example, the display control function 173 uses Formula (1) below to calculate a difference in the heart beats among the cross sections. In Formula (1), δHR represents a difference [%] in the heart rates among the cross sections. Furthermore, the maximum HR represents the maximum heart rate among the heart rates (HR) in the pieces of moving image data of the cross sections. Furthermore, the minimum HR represents the minimum heart rate among the heart rates (HR) in the pieces of moving image data of the cross sections.

$$\delta HR = 100*(\text{maximum HR} - \text{minimum HR})/\text{maximum HR} \quad (1)$$

The display control function 173 then displays the calculated δHR as the "HR_ERROR" on the display 103. In the example illustrated in FIG. 6, the display control function 173 displays HR_ERROR "10%" on the display 103 (see the lower right figure in FIG. 6).

For the "HR_ERROR", not only δHR but a difference in the end systolic times among cross sections may be used, for example. A difference in the end systolic times δESt among the cross sections is represented by Formula (2) below. In Formula (2), δESt represents a difference in the end systolic times [%] among cross sections. Furthermore, the maximum ESt represents the maximum end systolic time (ESt) among the end systolic times in the pieces of moving image data of the cross sections. Furthermore, the minimum ESt represents the minimum end systolic time (ESt) among the end systolic times in the pieces of moving image data of the cross sections.

$$\delta Est = 100*(\text{maximum ESt} - \text{minimum ESt})/\text{maximum ESt} \quad (2)$$

Furthermore, when "HR_ERROR" has exceeded a predetermined threshold, the display control function 173 may present information indicating that the threshold is exceeded to the operator. For example, when δHR has exceeded a predetermined threshold (20%, for example), the display control function 173 displays a predetermined sign in addition to the numerical value of the arrival time value displayed on each segment in the polar map. For example, the display control function 173 adds a sign "^" to a numerical value "XXX" and displays "^XXX" on the segment. Alternatively, the display control function 173 may display the numerical value "^XXX" in a different display color from the normal display color.

More specifically, the display control function 173 displays an index value (δHR or δESt) representing a difference in cardiac cycles in the collection periods of the cross sections. At this point, the display control function 173 may display the calculated index value constantly or at the time when the index value has exceeded the threshold. Furthermore, when the index value has exceeded the threshold, the display control function 173 may notify information indicating that the index value has exceeded the threshold (the above-described sign "^", an error message, or a notification sound, for example) or display the index value in an emphasized state (in a different color or in a bold font, for example).

Furthermore, the display control function 173 may display time curve analysis (TCA) of the strain values obtained in the cross sections. For example, the display control function 173 displays time curve analysis of the strain values in the A4C images (see the graph in the upper left in FIG. 6). Furthermore, the display control function 173 displays time curve analysis of the strain values in the A2C images (see the graph in the lower left in FIG. 6) and time curve analysis of the strain values in the A3C images (see the graph in the middle left in FIG. 6) in the same manner on the display 103.

Furthermore, the display control function 173 can display various parameters as numerical values. For example, besides the above-described "HR_ERROR", the display control function 173 displays parameters such as "GLPS_A3C", "GLPS_A4C", "GLPS_A2C", "GLPS_Avg", "ES", "AVC", and "HR_A3C" (see the lower right figure in FIG. 6). At this point, "GLPS" represents a global longitudinal PSS value on each section. More specifically, "GLPS_A3C" is a peak value that the global longitudinal strain value on the A3C plane has during a predetermined period. "GLPS_A4C" is a peak value that the global longitudinal strain value on the A4C plane has during a predetermined period. "GLPS_A2C" is a peak value that the global longitudinal strain value on the A2C plane has during a predetermined period. Furthermore, "GLPS_Ave" is an average value of "GLPS_A3C", "GLPS_A4C", and "GLPS_A2C". "ES" represents an average value of the time at which the interior volume of the cavity is the minimum in each cross section as an end systolic time. Furthermore, "AVC" is a closing time of the aortic valve. "HR_A3C" is a heart rate on the A3C plane.

Figure 7:
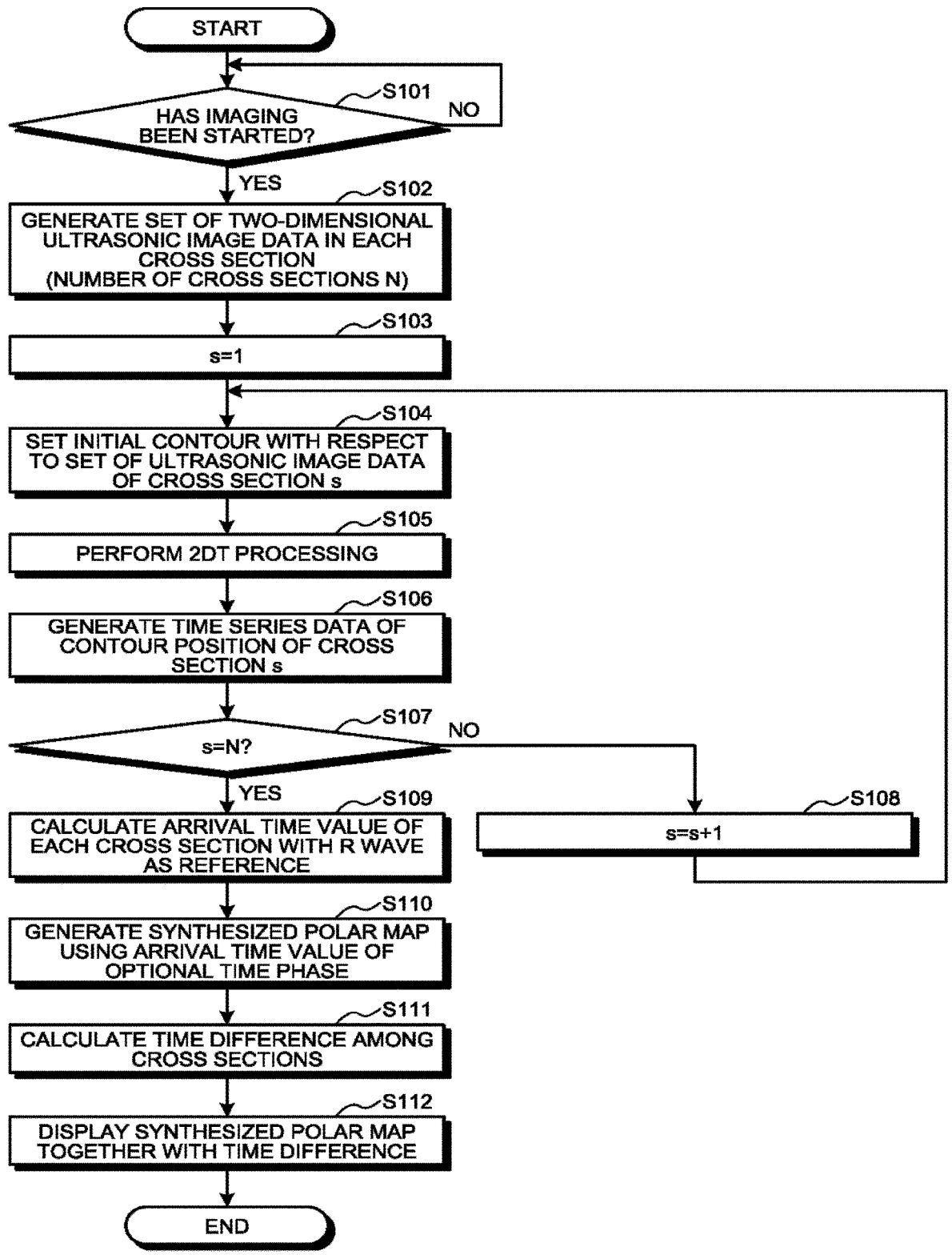
FIG. 7 is a flowchart illustrating a procedure of processing performed by the ultrasonic diagnostic apparatus according to the first embodiment.

FIG. 7 is a flowchart illustrating a procedure of processing performed by the ultrasonic diagnostic apparatus 1 according to the first embodiment. The procedure of processing illustrated in FIG. 7 is started when an instruction to start imaging of the subject P is received from the operator, for example.

At Step S101, it is determined whether imaging has been started. For example, the input device 102 receives an instruction to start imaging of the subject P from the operator and forwards the received instruction to the processing circuitry 170. Upon receiving the instruction forwarded from the input device 102, the processing circuitry 170 determines that the imaging has been started (Yes at Step S101) and starts processing at and after Step S102. It should be noted that when the imaging has not started (No at Step S101), processing at and after Step S102 is not started and each of the processing functions of the processing circuitry 170 is in a waiting state.

In the case of Yes at Step S101, the image generation circuitry 140 generates a set of two-dimensional ultrasonic image data in each cross section at Step S102. For example, the image generation circuitry 140 generates a plurality of ultrasonic image data along time series corresponding each of the A4C plane, the A2C plane, and the A3C plane. It should be noted that ultrasonic scan of the A4C plane, the A2C plane, and the A3C plane is performed in different times of day. Furthermore, in a case where ultrasonic scan of the A4C plane, the A2C plane, and the A3C plane is performed, the number of cross sections N=3.

At Step S103, the processing circuitry 170 sets "s=1". For example, the analysis information generation function 171 sets a set of ultrasonic image data of the A4C plane on the assumption that a cross section s=1.

At Step S104, the analysis information generation function 171 sets an initial contour with respect to the set of ultrasonic image data of the cross section s. For example, the analysis information generation function 171 sets a plurality of tracking points representing surfaces of the endocardium and the epicardium with respect to a piece of two-dimensional ultrasonic image data in the first frame of the A4C plane.

At Step S105, the analysis information generation function 171 performs 2DT processing. For example, the analysis information generation function 171 searches for a region that matches the best with the speckle pattern of the template data between two frames, thereby tracking to what position the template data is moved in the next frame.

At Step S106, the analysis information generation function 171 generates time series data of the contour position of the cross section s. For example, the analysis information generation function 171 generates time series data of the contour position of the left ventricle included in the A4C image.

At Step S107, the analysis information generation function 171 determines whether "s=N". At this point, in a case where "s" is not "N" (No at Step S107), the analysis information generation function 171 proceeds to processing at Step S108. By contrast, in a case where "s" is "N" (Yes at Step S107), the analysis information generation function 171 proceeds to processing at Step S109.

In the case of No at Step S107, the analysis information generation function 171 sets "s=s+1" at Step S108 and proceeds to processing at Step S104. More specifically, the analysis information generation function 171 determines that there still is a cross section to be processed with 2DT processing and proceeds to 2DT processing of the next cross section.

In the case of Yes at Step S107, the display image generation function 172 calculates the arrival time value of each cross section with an R-wave as a reference at Step S109. For example, the display image generation function 172 calculates the arrival time value with which the strain value at each point of the A4C image arrives at the level of 30% with respect to the peak value in one cardiac cycle of the point, with an R wave time phase as a reference time phase. Furthermore, the display image generation function 172 calculates the arrival time value in the same manner for each of the A2C image and the A3C image, with which the strain value at each point arrives at the level of 30% with respect to the peak value in one cardiac cycle of the point, with an R wave time phase as a reference time phase.

At Step S110, the display image generation function 172 generates a synthesized polar map using the arrival time value of an optional time phase. For example, the display image generation function 172 calculates the arrival time value at each point among the cross sections by interpolation processing in the circumferential direction using the arrival time value of each cross section. The display image generation function 172 then a pixel value corresponding to the calculated arrival time value of each point to generate a synthesized polar map.

At Step S111, the display control function 173 calculates a time difference in the heart beats among the cross sections. For example, as an index value of fluctuation in one cardiac cycle among a plurality of cross sections, the display control function 173 calculates a difference δHR [%] in the heart rates among the cross sections.

At Step S112, the display control function 173 displays the synthesized polar map together with a time difference. For example, the display control function 173 displays the synthesized polar map generated by the display image generation function 172 on the display 103 and displays the calculated δHR [%] as "HR_ERROR".

As described above, in the ultrasonic diagnostic apparatus 1 according to the first embodiment, with respect to pieces of image data of a plurality of cross sections passing through the heart of a subject that have been collected by ultrasonically scanning each of the cross sections for a period of at least one heart beat, the analysis information generation function 171 performs tracking processing including two-dimensional pattern matching to generate pieces of analysis information in each of which the cardiac wall motion of the heart in each section is analyzed. The display image generation function 172 then matches the time phases of the pieces of analysis information of the cross sections and maps the pieces of analysis information of the cross sections with the matched time phases on a predetermined polar coordinate system, thereby generating a polar image. The display control function 173 displays the generated polar map. With this configuration, the ultrasonic diagnostic apparatus 1 according to the first embodiment can display a polar map in a manner matching the time phases of the pieces of image data of a plurality of cross sections that have been separately collected.

For example, conventionally, in a case where a synthesized polar map is displayed based on a plurality of cross sections collected in different times of day, an index value that does not depend on a time is defined, whereby the analysis results from the cross sections are synthesized without consideration for the differences in the time of day to display the synthesized polar map. In such a display mode, although information related to the temporal change of a wall motion (time information) is originally obtained as the analysis results of the cross sections, during the course of synthesizing the analysis results of the cross sections, the time information is lost. In other words, conventional techniques have not been able to display a synthesized polar map based on time information from the analysis results of the cross sections that have been collected in different times of day.

By contrast, the ultrasonic diagnostic apparatus 1 according to the first embodiment matches the time phases of the pieces of image data of a plurality of cross sections that have been separately collected and then synthesizes the analysis results of the cross sections to generate a synthesized polar map. Specifically, the ultrasonic diagnostic apparatus 1 matches the reference time phases of the analysis results of the cross sections to an R-wave time phase and then calculates the arrival time values to generate a synthesized polar map, based on the calculated arrival time values. With this configuration, with the ultrasonic diagnostic apparatus 1 according to the first embodiment, even the pieces of image data of a plurality of cross sections that have been separately collected can be reflected on a synthesized polar map, without losing time information related to the temporal change of a wall motion. Specifically, even when the lengths of one heart beat or the frame rates in the pieces of analysis information of the cross sections that have been collected in different times of day are different, the ultrasonic diagnostic apparatus 1 can generate a synthesized polar map and display the generated synthesized polar map.

Furthermore, in a case where the time fluctuation is small among the cross sections, the ultrasonic diagnostic apparatus 1 according to the first embodiment considers that the time phases of the cross sections are substantially matched and obtains the arrival time value of each cross section based on an R-wave time phase. With this, the ultrasonic diagnostic apparatus 1 can display a synthesized polar map without losing time information related to the temporal change of a wall motion, with a simple configuration.

Furthermore, the ultrasonic diagnostic apparatus 1 according to the first embodiment displays an index value of fluctuation among each of a plurality of cross sections. With this configuration, the ultrasonic diagnostic apparatus 1 can present the reliability of the displayed synthesized polar map to the operator.

Modification of the First Embodiment

Even when the pieces of analysis information of all the cross sections to be synthesized have not been collected, the ultrasonic diagnostic apparatus 1 generates a synthesized polar map sequentially from the pieces of analysis information of the cross sections, for which the wall motion analysis has been completed, to update as appropriate the synthesized polar map every time a wall motion analysis operation has been completed.

More specifically, the display image generation function 172 generates a polar map based on the piece of analysis information of a cross section, for which the wall motion analysis has been completed by the analysis information generation function 171, out of a plurality of cross sections. Furthermore, once the wall motion analysis operation for another cross section has been newly completed by the analysis information generation function 171, the display image generation function 172 updates the generated polar map based on the piece of analysis information of that another cross section. Furthermore, every time the polar map is updated by the display image generation function 172, the display control function 173 displays the updated polar map.

Figure 8:
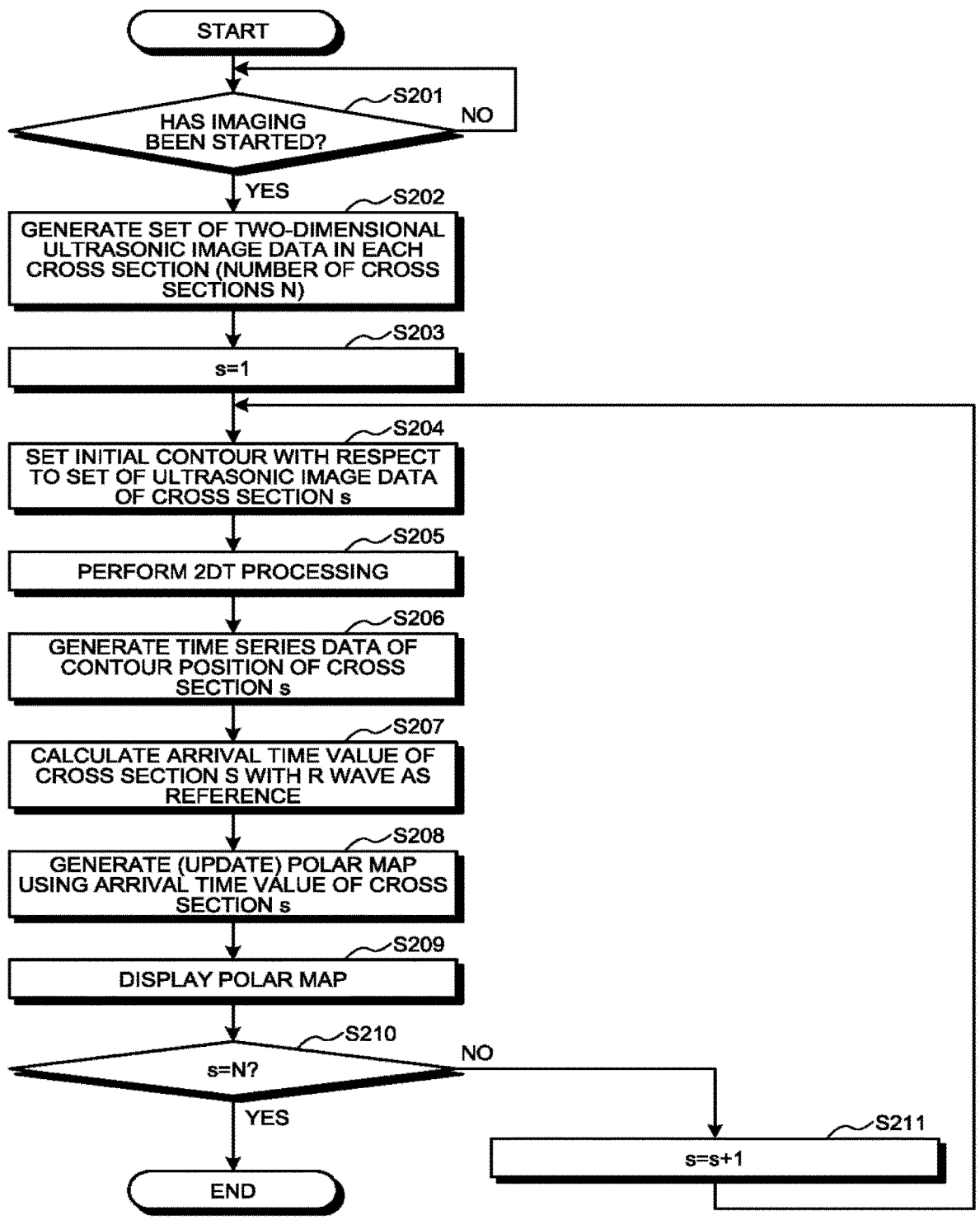
FIG. 8 is a flowchart illustrating a procedure of processing performed by an ultrasonic diagnostic apparatus according to a modification of the first embodiment.

FIG. 8 is a flowchart illustrating a procedure of processing performed by the ultrasonic diagnostic apparatus 1 according to a modification of the first embodiment. In the procedure of processing illustrated in FIG. 8, the processing from Step S201 to Step S206 are the same as that from Step S101 to Step S106 illustrated in FIG. 7, and the description thereof will be omitted.

At Step S207, the display image generation function 172 calculates the arrival time value of a cross section s with an R-wave as a reference. For example, the display image generation function 172 calculates the arrival time value with which the strain value at each point in an A4C image arrives at the level of 30% with respect to the peak value in one cardiac cycle of the point, with an R wave time phase as a reference time phase.

At Step S208, the display image generation function 172 uses the arrival time of the cross section s to generate a synthesized polar map. For example, the display image generation function 172 allocates the arrival time values at the points on the A4C image partially to a polar map.

At Step S209, the display control function 173 displays the polar map. For example, the display control function 173 causes the display 103 to display the polar map on which the arrival time values at the points on the A4C map are allocated partially.

At Step S210, the display control function 173 determines whether "s=N". At this point, in a case where "s" is not "N" (No at Step S210), the display control function 173 proceeds to processing at Step S211. By contrast, in a case where "s" is "N" (Yes at Step S210), the display control function 173 ends the processing in FIG. 8.

In the case of No at Step S210, the display control function 173 sets "s=s+1" at Step S211 and proceeds to processing at Step S204. More specifically, the display control function 173 determines that there still is a cross section to be processed with 2DT processing and proceeds to 2DT processing of the next cross section.

Figure 9:
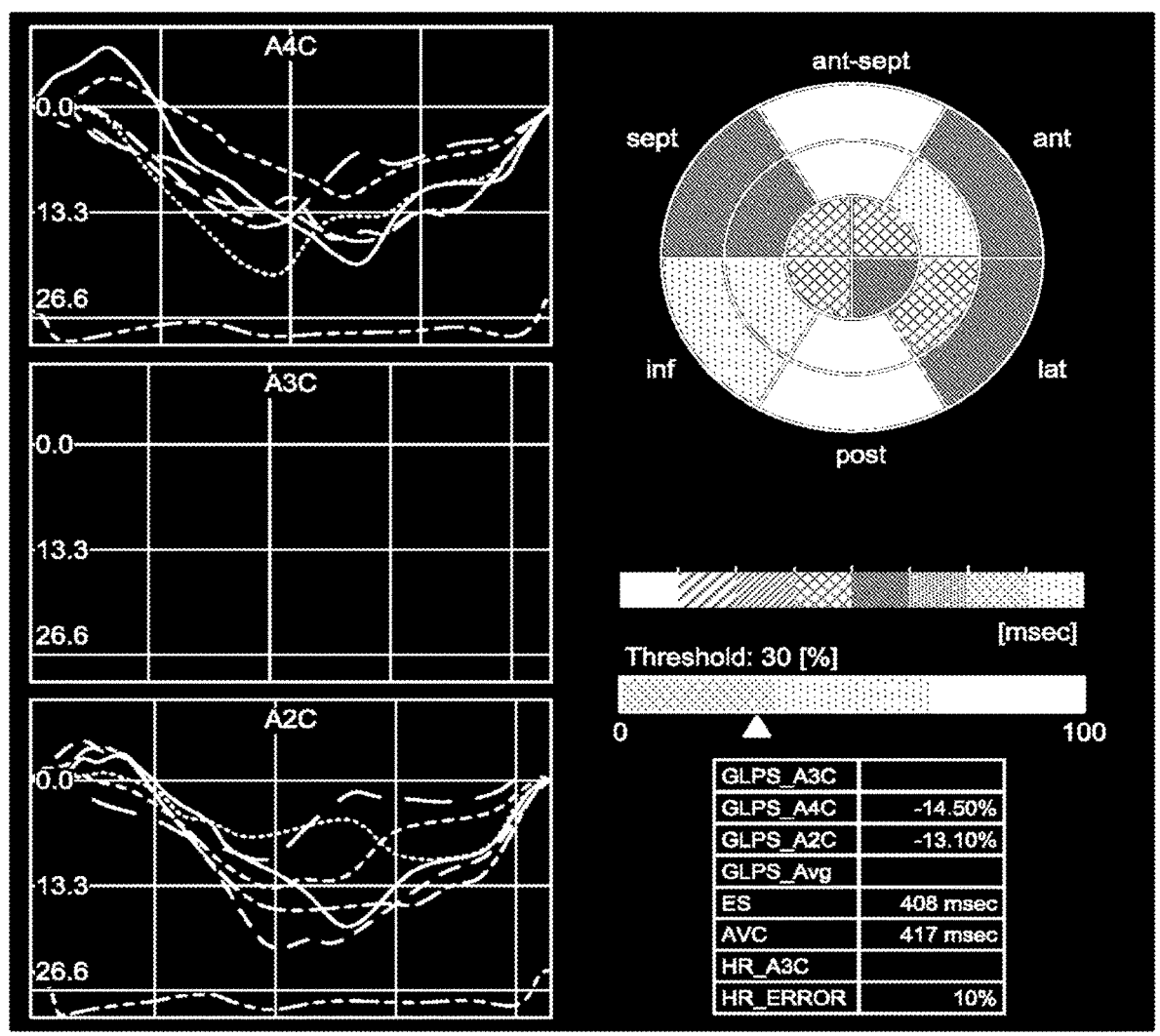
FIG. 9 is a diagram for explaining the processing performed by the ultrasonic diagnostic apparatus according to the modification of the first embodiment.

FIG. 9 is a diagram for explaining the processing performed by the ultrasonic diagnostic apparatus 1 according to the modification of the first embodiment. FIG. 9 exemplifies a display image displayed in a case where out of the A4C plane, A2C plane, and the A3C plane, pieces of analysis information of the A4C plane and the A2C plane are generated by 2DT.

As illustrated in FIG. 9, the display image generation function 172 generates a polar map based on the pieces of analysis information of the A4C plane and the A2C plane by means of the analysis information generation function 171. Specifically, the display image generation function 172 allocates a pixel value corresponding to the arrival time value of each point on the A4C image to each of the segments of the septum (sept) and the lateral wall (lat) as well as allocates a pixel value corresponding to the arrival time value of each point on the A2C image to each of the segments of the anterior wall (ant) and the inferior wall (inf) to generate a synthesized polar map. The display control function 173 then causes the display 103 to display the synthesized polar map generated by the display image generation function 172. It should be noted that in FIG. 9, because the analysis operations for the A3C plane have not been completed, no pixel value is allocated to each of the points of the anteroseptal (ant-sept) and the posterior wall (post). Furthermore, the time curve analysis graph of strain values for the A3C plane is still blank.

Thereafter, when the analysis operations have been completed by the analysis information generation function 171, for example, the display image generation function 172 updates the synthesized polar map in FIG. 9 and generates the synthesized polar map illustrated in FIG. 6. It should be noted that the display image generation function 172 also generates items other than a display image based on the pieces of analysis information of the A3C plane. The display control function 173 then causes the display 103 to display the synthesized polar map updated by the display image generation function 172.

As described above, even when the pieces of analysis information of all the cross sections to be synthesized have not been collected, the ultrasonic diagnostic apparatus 1 generates a synthesized polar map sequentially from the pieces of analysis information of the cross sections, for which the wall motion analysis has been completed, to update as appropriate the synthesized polar map every time a wall motion analysis operation has been completed. The present modification has an effect to make it easy for the operator to determine the next cross section to be analyzed, because the operator can clearly distinguish at a glance between a cross section for which the analysis operation has been completed and a cross section for which the analysis operation has not been completed.

Second Embodiment

In a second embodiment, a case is described where the influence of a difference in the cardiac time phases among the cross sections is corrected to achieve higher accuracy in synthesizing the pieces of analysis information of the cross sections.

An ultrasonic diagnostic apparatus 1 according to the second embodiment includes the same configuration as the ultrasonic diagnostic apparatus 1 illustrated in FIG. 1, and a part of the processing performed by the display image generation function 172 is different. For this reason, in the second embodiment, the points different from those in the first embodiment will be mainly described, and the descriptions of the points having similar functions to those configurations described in the first embodiment will be omitted.

The display image generation function 172 according to the second embodiment corrects the pieces of analysis information of the cross sections with a predetermined interval of a time between two cardiac time phases and maps the pieces of analysis information of the cross sections after correction on the predetermined polar coordinate system to generate a polar map.

For example, the display image generation function 172 firstly sets a reference time Tc serving as a reference for correcting the pieces of analysis information of the cross sections. This reference time is a time set for uniforming the times of one cardiac cycle or the times required for the systolic period (end systolic time) of the cross sections. More specifically, the display image generation function 172 normalizes the times of one cardiac cycle or the end systolic times of the cross sections to the reference time Tc.

For example, the display image generation function 172 selects a cross section with which the heart rate HR [bpm] is a median value HRm out of the cross sections and sets the time of one cardiac cycle of the selected cross section as the reference time Tc. For example, the reference time Tc [msec] is represented by Formula (3) below.

$$Tc=1000/(HRm/60) \tag{3}$$

Thereafter, the display image generation function 172 calculates a correction coefficient Tk for correcting the pieces of analysis information of the cross sections. The correction coefficient Tk is represented by Formula (4) below. It should be noted that in Formula (4), Tn represents a time subjected to comparison for correction, and in this example, corresponds to the time of one cardiac cycle of each cross section.

$$Tk=Tc/Tn \quad (4)$$

More specifically, when the time of one cardiac cycle of the A4C plane is Tn1, the correction coefficient Tk1 of the A4C plane is represented by "Tk1=Tc/Tn1". Furthermore, the time of one cardiac cycle of the A2C plane is Tn2, the correction coefficient Tk2 of the A2C plane is represented by "Tk2=Tc/Tn2". Furthermore, the time of one cardiac cycle of the A3C plane is Tn3, the correction coefficient Tk3 of the A3C plane is represented by "Tk3=Tc/Tn3".

Thereafter, the display image generation function 172 corrects the arrival time value of each cross section by multiplying the arrival time value of the cross section by the correction coefficient of the cross section. More specifically, the arrival time value AI1'(td1) of the A4C plane after correction is represented by "AI1'(td1)=Tk1*AI1(td1)". Furthermore, the arrival time value AI2'(td2) of the A2C plane after correction is represented by "AI2'(td2)=Tk2*AI2(td2)". Furthermore, the arrival time value AI3'(td3) of the A3C plane after correction is represented by "AI3'(td3)=Tk3*AI3(td3)". It should be noted that the processing performed by the display image generation function 172 to calculate the arrival time values AI1'(td1), AI2'(td2), and AI3'(td3) is the same as that described in the first embodiment.

Thereafter, the display image generation function 172 uses the arrival time values AI1'(td1), AI2'(td2), and AI3'(td3) after correction to generate a synthesized polar map.

Figure 10:
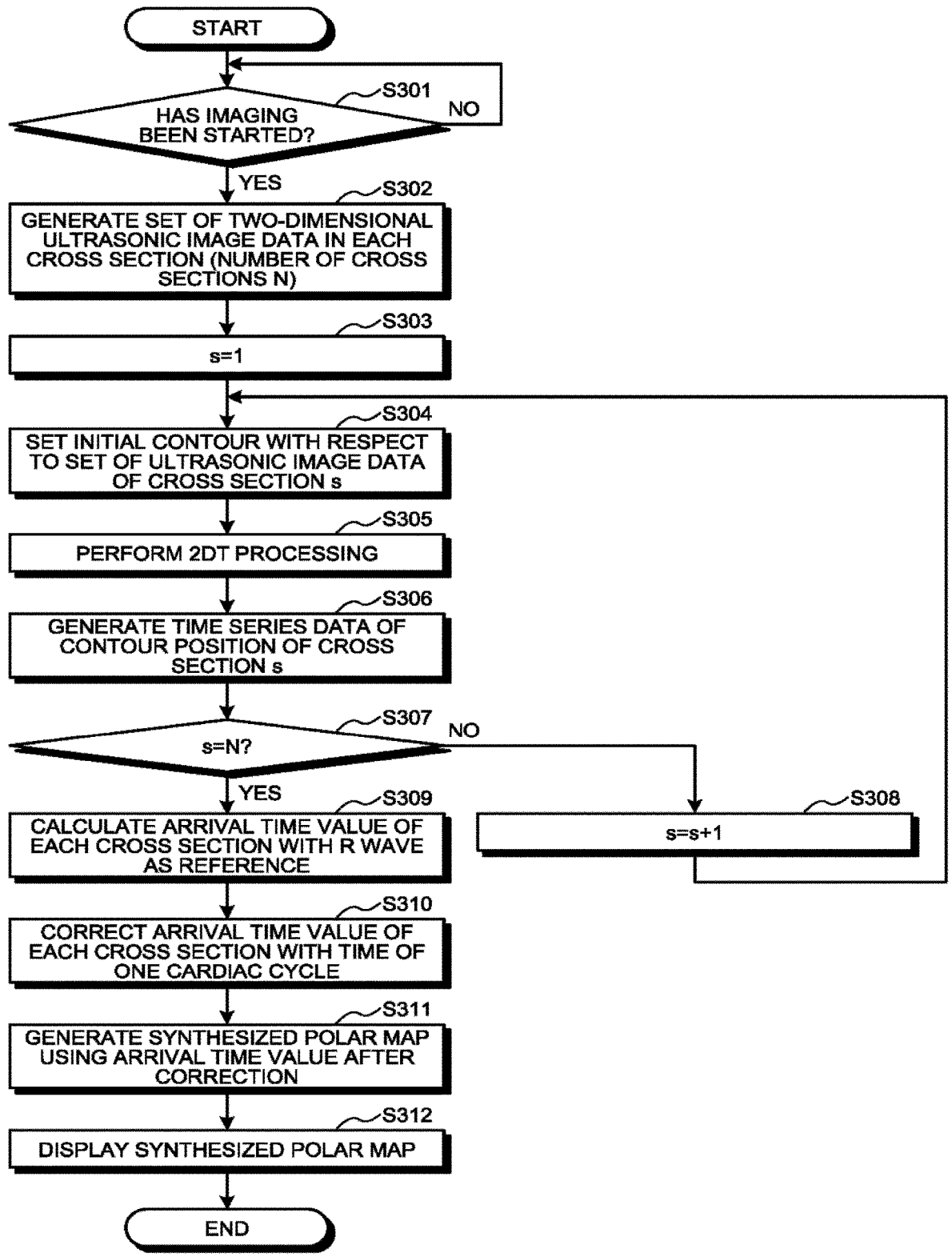
FIG. 10 is a flowchart illustrating a procedure of processing performed by an ultrasonic diagnostic apparatus according to a second embodiment.

FIG. 10 is a flowchart illustrating a procedure of processing performed by the ultrasonic diagnostic apparatus 1 according to the second embodiment. In the procedure of processing illustrated in FIG. 10, the processing from Step S301 to Step S309 are the same as that from Step S101 to Step S109 illustrated in FIG. 7, and the description thereof will be omitted. More specifically, the processing performed by the display image generation function 172 to calculate the arrival time value AI1(td1) of an A4C image, the arrival time value AI2(td2) of the A2C image, and the arrival time value AI3(td3) of the A3C image as an R-wave as a reference is the same as that described in the first embodiment.

At Step S310, the display image generation function 172 corrects the arrival time value of each cross section with the time of one cardiac cycle. For example, the display image generation function 172 calculates the correction coefficient Tk of each cross section and multiplies the arrival time value AI(td) of each cross section by the calculated correction coefficient Tk to correct the arrival time value of each cross section.

At Step S311, the display image generation function 172 generates a synthesized polar map using the arrival time values after correction. For example, the display image generation function 172 generates a synthesized polar map using the arrival time values AI1'(td1), AI2'(td2), and AI3'(td3) after correction.

At Step S312, the display control function 173 causes the display 103 to display a synthesized polar map synthesized by the display image generation function 172.

As described above, the ultrasonic diagnostic apparatus 1 according to the second embodiment can correct the influence of a difference in the cardiac time phases among the cross sections to achieve higher accuracy in synthesizing the pieces of analysis information of the cross sections.

The embodiment is not limited to the example described above. For example, the reference time Tc may be given by an average value HRave of heart rate HR of the cross sections. In this case, the reference time Tc is represented by Formula (5) below.

$$Tc=1000/(HRave/60) \quad (5)$$

Alternatively, instead of a time of one cardiac cycle, as an end systolic time, an ES time as an average value of the time at which the interior volume of the cavity is the minimum in each cross section may be given. Furthermore, an AVC time may be given as the reference time Tc. In both cases above, the time at which the interior volume of the cavity is the minimum in each cross section may be given as a time Tn subjected to comparison for correction.

Fluctuation of HR is generated with a time required for the systolic period and a time required for the diastolic period extended and shortened. However, it is thought the direction in which the AI values are extended and shortened is basically the same as the fluctuation direction of these times required and changes in correlation with the time of cardiac cycle. Because an AI value captures the systolic timing (as regional contraction), it is thought that the correlation with the time required for the systolic period is higher. For this reason, as a reference time Tc, an ES time and An AVC time are preferably used to increase the correction accuracy.

Furthermore, in the second embodiment, because a plurality of applicable values are presumable as the reference time Tc, it is preferable to indicate what kind of reference time Tc is selected, the value of the reference time Tc, and the value of the correction coefficient Tk of each cross section and thereby present to what degree the correction has been made on what cross section.

Furthermore, as described in the first embodiment, as the index value of the reliability of the synthesized polar map, "HR_ERROR" may be used.

Third Embodiment

In a third embodiment, interpolation processing is performed such that the time interval of the pieces of analysis information of the cross sections are a fixed time interval, whereby a moving image of a synthesized polar map is generated from pieces of image data of a plurality of cross sections that have been collected in different times of day.

An ultrasonic diagnostic apparatus 1 according to the third embodiment includes the same configuration as the ultrasonic diagnostic apparatus 1 illustrated in FIG. 1, and a part of the processing performed by the display image generation function 172 and the display control function 173 is different. For this reason, in the third embodiment, the points different from those in the first embodiment will be mainly described, and the descriptions of the points having similar functions to those configurations described in the first embodiment will be omitted.

The display image generation function 172 according to the third embodiment performs interpolation processing such that time intervals of the pieces of analysis information of the cross sections are fixed time intervals based on a predetermined length of a time between two cardiac time phases and maps pieces of analysis information out of the pieces of analysis information of the cross sections after correction with the same time phases on the predetermined polar coordinate system to generate a polar map with a frame rate corresponding to the predetermined time intervals. It should be noted that the analysis information generation function 171 generates the piece of analysis information of each cross section with the time interval corresponding to the frame rate of the cross section. The display control function 173 according to the third embodiment displays a polar map with a predetermined frame rate as a moving image.

Figure 11:
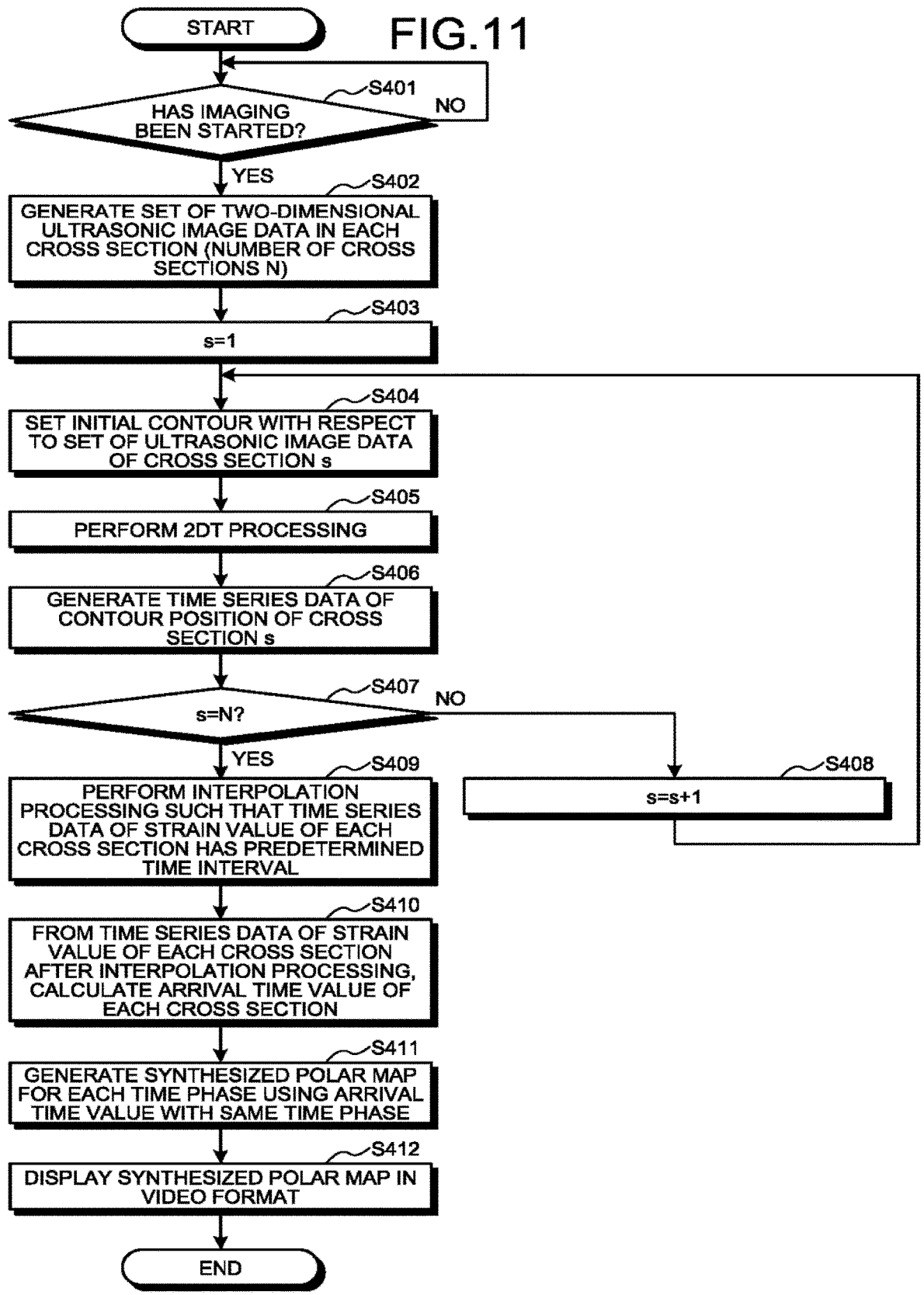
FIG. 11 is a flowchart illustrating a procedure of processing performed by an ultrasonic diagnostic apparatus according to a third embodiment.

FIG. 11 is a flowchart illustrating a procedure of processing performed by the ultrasonic diagnostic apparatus 1 according to the third embodiment. In the procedure of processing illustrated in FIG. 11, the processing from Step S401 to Step S408 are the same as that from Step S101 to Step S108 illustrated in FIG. 7, and the description thereof will be omitted.

At Step S409, the display image generation function 172 performs interpolation processing such that the time series data of the strain value of each cross section has a predetermined time interval.

Figure 12:
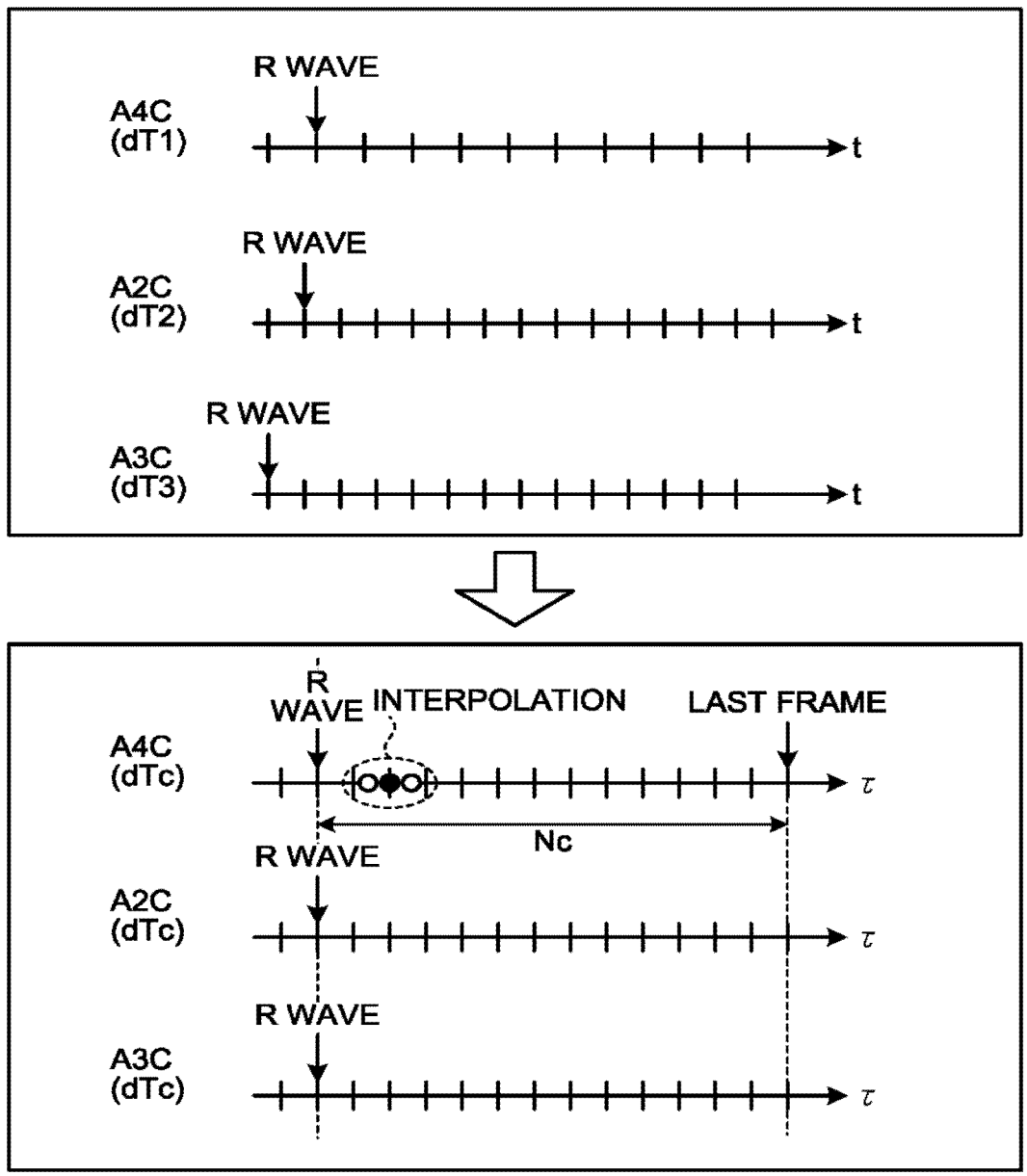
FIG. 12 is a diagram for explaining interpolation processing of a display image generation function according to the third embodiment.

FIG. 12 is a diagram for explaining interpolation processing of the display image generation function 172 according to the third embodiment. FIG. 12 exemplifies the processing of the display image generation function 172 in a case where interpolation processing is performed with the time phases of the A4C plane, the A2C plane, and the A3C plane matched among each other. In the upper figure in FIG. 12, the horizontal axis corresponds to a time t (frame of the moving image data). Furthermore, in the upper figure in FIG. 12, the frame interval of the moving image data of the A4C image is "dT1", the frame interval of the moving image data of the A2C image is "dT2", and the frame interval of the moving image data of the A3C image is "dT3". At this example case, dT3<dT2<dT1. Furthermore, in the lower diagram in FIG. 12, the horizontal axis corresponds to a time t (frame of the moving image data after correction). Furthermore, in the lower figure in FIG. 12, the frame interval of the moving image data of the cross sections after correction is "dTc". Furthermore, the time of one cardiac cycle included in the moving image data after correction is "Nc". In the present embodiment, a correction method using the reference time Tc described in the second embodiment is preferably used to correct a time among cross sections. In this case, the Nc is firstly calculated. In view of matching the times of the last frames, correction of the times is made based on the time of one cardiac cycle. Next, the dTc is determined by dividing the Nc equally. To cite another example, the most average frame interval among the cross sections (dT2 being a median value is preferably selected) is used to obtain dTc firstly. Next, a method can be cited with which the time of one cardiac cycle in the piece of data of the cross section from which the dTc has been obtained is determined as the Nc.

As illustrated in FIG. 12, for example, the display image generation function 172 acquires a time curve S(t) of a local strain value of each cross section. Specifically, the display image generation function 172 acquires a time curve S1(t) of a local strain value of the A4C plane, a time curve S2(t) of the A2C plane, and a time curve S3(t) of the A3C plane. At this point, the time intervals of the time curve S1(t) is dT1, the time intervals of the time curve S2(t) is dT2, the time intervals of the time curve S3(t) is dT3.

The display image generation function 172 then sets the time interval dTc and the time Nc of one cardiac cycle which are fixed by interpolation processing and performs interpolation processing on the time curves of the strain values of the cross sections in the time direction at each point. With this, the display image generation function 172 generates S'(τ) obtained by interpolation of the time curves of the local strain values of the cross sections. Specifically, the display image generation function 172 generates a time curve S1'(τ) of the A4C plane after correction, a time curve S2'(τ) of the A2C plane after correction, and a time curve S3'(τ) of the A3C plane after correction. At this point, with respect to each of the time curves S1'(τ), S2'(τ), and S3'(τ) of the cross sections after correction, the time interval is dTc and the time of one cardiac cycle is Nc.

At Step S410, the display image generation function 172 calculates arrival time values AI1"(τ), AI2"(τ), and AI3"(τ) of the cross sections from the time curves S1'(τ), S2'(τ), and S3'(τ) of the strain values of the cross sections after correction, as each of the R waves as a reference.

At Step S411, the display image generation function 172 generates a synthesized polar map for each time phase using the arrival time values with the same time phases. For example, the display image generation function 172 generates a moving image of the synthesized polar map using the arrival time values AI1"(τ), AI2"(τ), and AI3"(τ) of the cross sections.

At Step S412, the display control function 173 displays the synthesized polar map generated by the display image generation function 172 in a video format.

As described above, the ultrasonic diagnostic apparatus 1 according to the third embodiment enables display of a moving image of a synthesized polar map from the pieces of image data of a plurality of cross sections which have been collected in different times of day.

As an index of a wall motion displayed on a synthesized polar map as a piece of moving image data, besides the arrival time value, a strain value may be applied, for example. Furthermore, by changing inputs for the time curves to be processed with the interpolation processing, an optional physical index provided in 2DT can be selected. For example, not only a strain value, but a displacement, a strain rate being a time differential of these, and a velocity may be used as the physical index. Furthermore, for example, a PSS value may be obtained from a time curve of a strain value after correction, and a synthesized polar map using the PSS value may be displayed as a still image.

Furthermore, in the third embodiment, a case has been described where the analysis information generation function 171 generates the piece of the analysis information of each cross section at the time interval corresponding to the frame rate of the cross section. However, the embodiment is not limited thereto. For example, the analysis information generation function 171 may generate a moving image value of each cross section by inter-frame interpolation (publicly known technique) and generate a piece of analysis information of a cross section by 2DT processing using the generated moving image value. Furthermore, as described in the first embodiment, as an index value of the reliability of the synthesized polar map, "HR_ERROR" may be displayed.

Fourth Embodiment

Furthermore, in the embodiments described above, a case has been described in which a synthesized polar map is displayed. However, the embodiments are not limited thereto. For example, the ultrasonic diagnostic apparatus 1 may display a display image representing the pieces of analysis information of the cross sections as well as a difference in the times of the cross sections.

An ultrasonic diagnostic apparatus 1 according to a fourth embodiment includes the same configuration as the ultrasonic diagnostic apparatus 1 illustrated in FIG. 1, and a part of the processing performed by the display control function 173 is different. For this reason, in the fourth embodiment, the points different from those in the first embodiment will be mainly described, and the descriptions of the points having similar functions to those of the configurations described in the first embodiment will be omitted. It should be noted that the ultrasonic diagnostic apparatus 1 according to the fourth embodiment may not include the display image generation function 172.

The display control function 173 according to the fourth embodiment matches the time phases of the pieces of analysis information of the cross sections and displays the pieces of analysis information of the cross sections with the time phases thereof matched as well as an index value representing a difference in the cardiac cycles in the collection periods of the cross sections.

Figure 13:
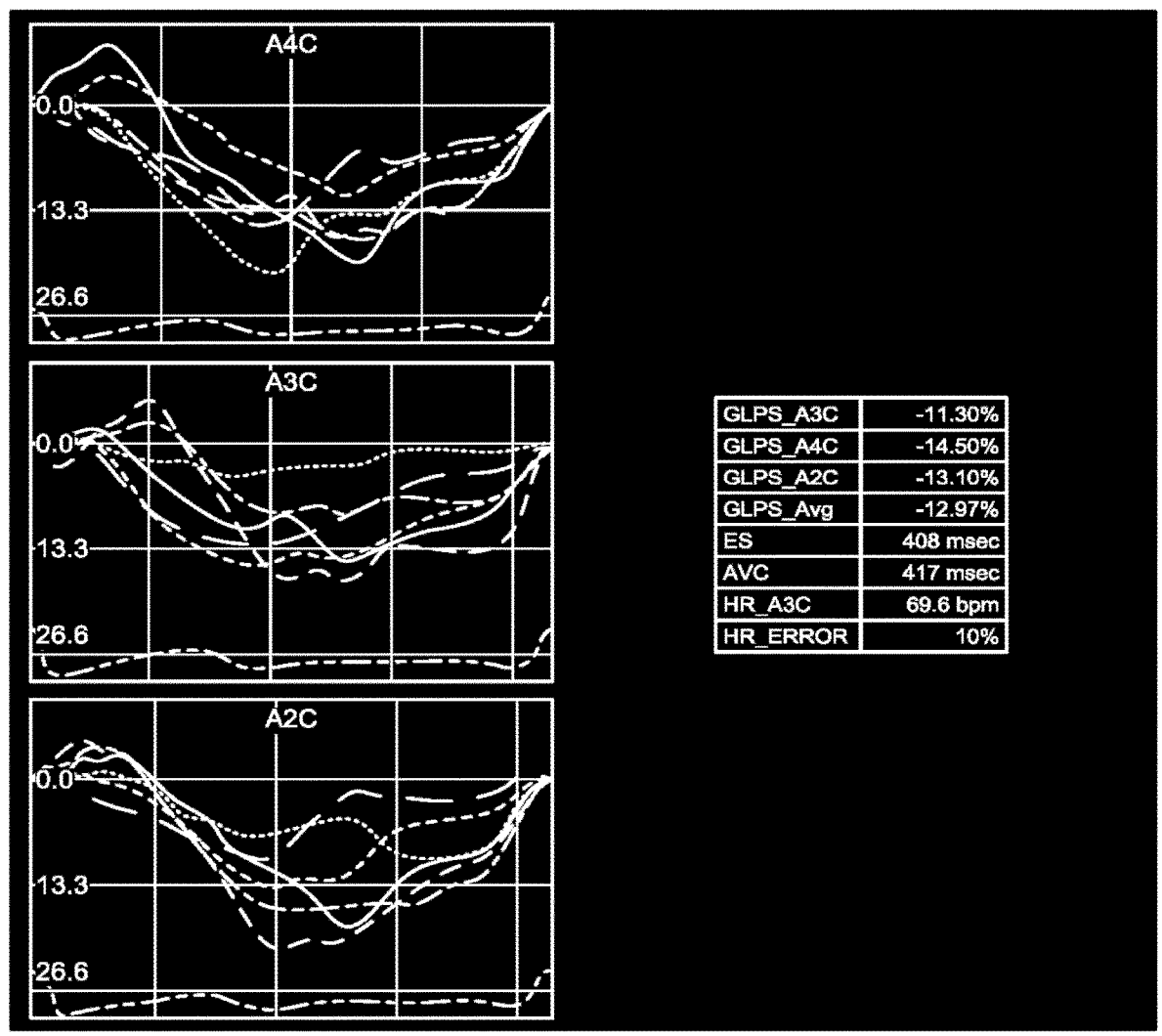
FIG. 13 is a diagram for explaining processing of a display control function according to a fourth embodiment.

FIG. 13 is a diagram for explaining processing of the display control function 173 according to the fourth embodiment. FIG. 13 exemplifies a display screen displayed on the display 103 by means of the processing of the display control function 173.

As illustrated in FIG. 13, the display control function 173 matches the time phases of the pieces of analysis information of the cross sections in different times of day as a predetermined cardiac time phase as a reference. For example, the display control function 173 matches the time changes of the strain values obtained from the cross sections at a certain time phase (the time phase of an R-wave, for example). The display control function 173 then generates the time curves (graphs) of the cross sections in a state in which the time changes are matched at the certain time phase. The display control function 173 then causes the display 103 to display the time curve of each cross section. For example, the display control function 173 causes the display 103 to display the time curve of a strain value on the A4C (the upper left graph in FIG. 13), the time curve of a strain value on the A3C (the middle left graph in FIG. 13), and the time curve of a strain value on the A2C (the lower left graph in FIG. 13). At this point, with respect to the time curve of the cross sections A4C, A3C, and A2C, the direction of the time axis in each graph matches among each other at a certain time phase (the time phase of an R wave). It should be noted that the detailed description of the time curves of the cross sections is the same as in the first embodiment and thus will be omitted.

Furthermore, the display control function 173 displays δHR in the collection periods of the cross sections. For example, the display control function 173 uses Formula (1) described above to calculate δHR as an index value representing a difference in the cardiac cycles. The display control function 173 then causes the display 103 to display the calculated δHR as "HR_ERROR". In the example illustrated in FIG. 13, the display control function 173 causes the display 103 to display HR_ERROR "10%" (the table on the right in FIG. 13).

At this point, the display control function 173 may display the calculated δHR constantly or at the time when the δHR has exceeded the threshold. Furthermore, when the δHR has exceeded the threshold, the display control function 173 may notify information indicating that the δHR has exceeded the threshold (the above-described sign "^", an error message, or a notification sound, for example) or display the δHR in an emphasized state (in a different color or in a bold font, for example). It should be noted that the detailed description of the calculation of the δHR is the same as in the first embodiment and thus will be omitted.

As described above, the display control function 173 displays the time curves of the cross sections as well as the δHR among the cross sections. It should be noted that the above-described contents of the processing performed by the display control function 173 is merely an example, and the embodiment is not limited thereto. For example, the display control function 173 may display not only the δHR but the δESt (calculated by Formula (2) described above) as an index value representing a difference in the cardiac cycle.

For example, the display control function 173 may display not only the time curves but an optional graph such as a bar graph at a certain point (time phase). Furthermore, the display control function 173 may display a graph related to not only a strain value but an optional parameter such as an arrival time value or a volume of cavity. Furthermore, the display control function 173 may display not only a graph but a numerical value of an optional parameter. In other words, the display control function 173 can display the pieces of analysis information of the cross sections as a graph or a numerical value.

Figure 14:
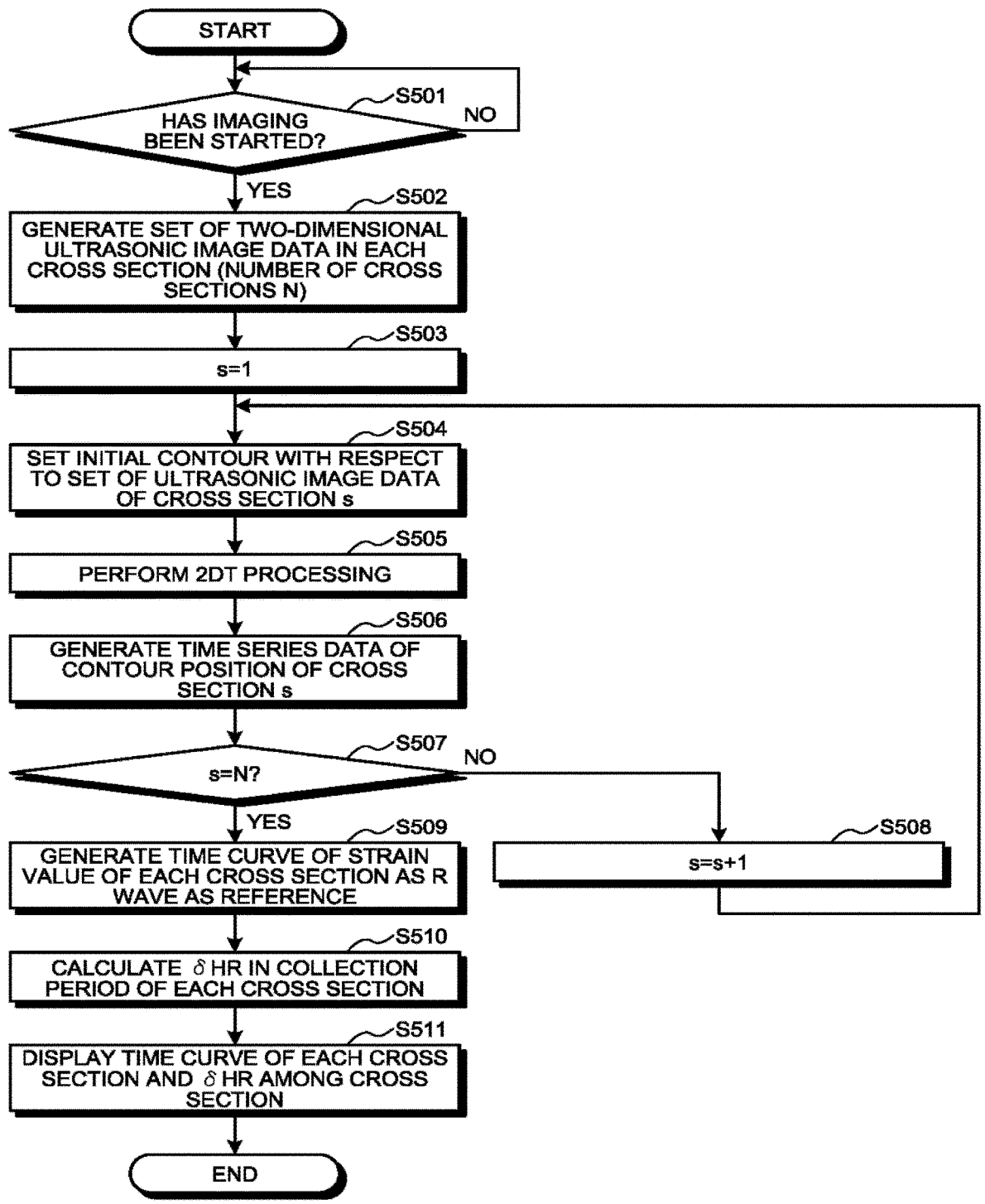
FIG. 14 is a flowchart illustrating a procedure of processing performed by an ultrasonic diagnostic apparatus according to the fourth embodiment.

FIG. 14 is a flowchart illustrating a procedure of processing performed by the ultrasonic diagnostic apparatus 1 according to the fourth embodiment. In the procedure of processing illustrated in FIG. 14, the processing from Step S501 to Step S508 are the same as that from Step S501 to Step S508 illustrated in FIG. 7, and the description thereof will be omitted.

At Step 3509, the display control function 173 generates the time curve of the strain value of each cross section as an R wave as a reference. With this, the display control function 173 generates graphs of which the time axis directions are matched with an R wave, with respect to the cross sections A4C, A3C, and A2C.

At Step S510, the display control function 173 calculates δHR in the collection periods of the cross sections.

At Step S511, the display control function 173 calculates the time curves of the cross sections and the δHR among the cross sections.

As described above, with respect to pieces of image data of a plurality of cross sections passing through the heart of a subject that have been collected by ultrasonically scanning each of the cross sections for a period of at least one heart beat, the ultrasonic diagnostic apparatus 1 according to the fourth embodiment performs tracking processing including two-dimensional pattern matching to generate pieces of analysis information in each of which the cardiac wall motion of the heart in each section is analyzed. Furthermore, the ultrasonic diagnostic apparatus 1 matches the time phases of the pieces of analysis information of the cross sections and displays the pieces of analysis information of the cross sections with the time phases thereof matched as well as an index value representing a difference in the cardiac cycle in the collection periods of the cross sections. With this configuration, the ultrasonic diagnostic apparatus 1 according to the fourth embodiment can display an index value representing a difference in the cardiac cycle when displaying the pieces of analysis information in a manner matching the time phases of pieces of image data of the cross sections that have been separately collected.

Modification of the Fourth Embodiment

The details described in the fourth embodiment are merely an example, and the embodiment is not limited to the description above. For example, the ultrasonic diagnostic apparatus 1 according to the fourth embodiment may display the pieces of analysis information of the cross sections and an index value representing a difference in the cardiac cycles as well as pieces of image data of the cross sections as inputs.

More specifically, the display control function 173 according to a modification of the fourth embodiment further displays pieces of image data of the cross sections for which the tracking processing has been performed. Specifically, the display control function 173 causes the display 103 to display pieces of image data of a plurality of cross sections passing through the heart of a subject that have been collected by ultrasonically scanning each of the cross sections for a period of at least one heart beat.

Figure 15:
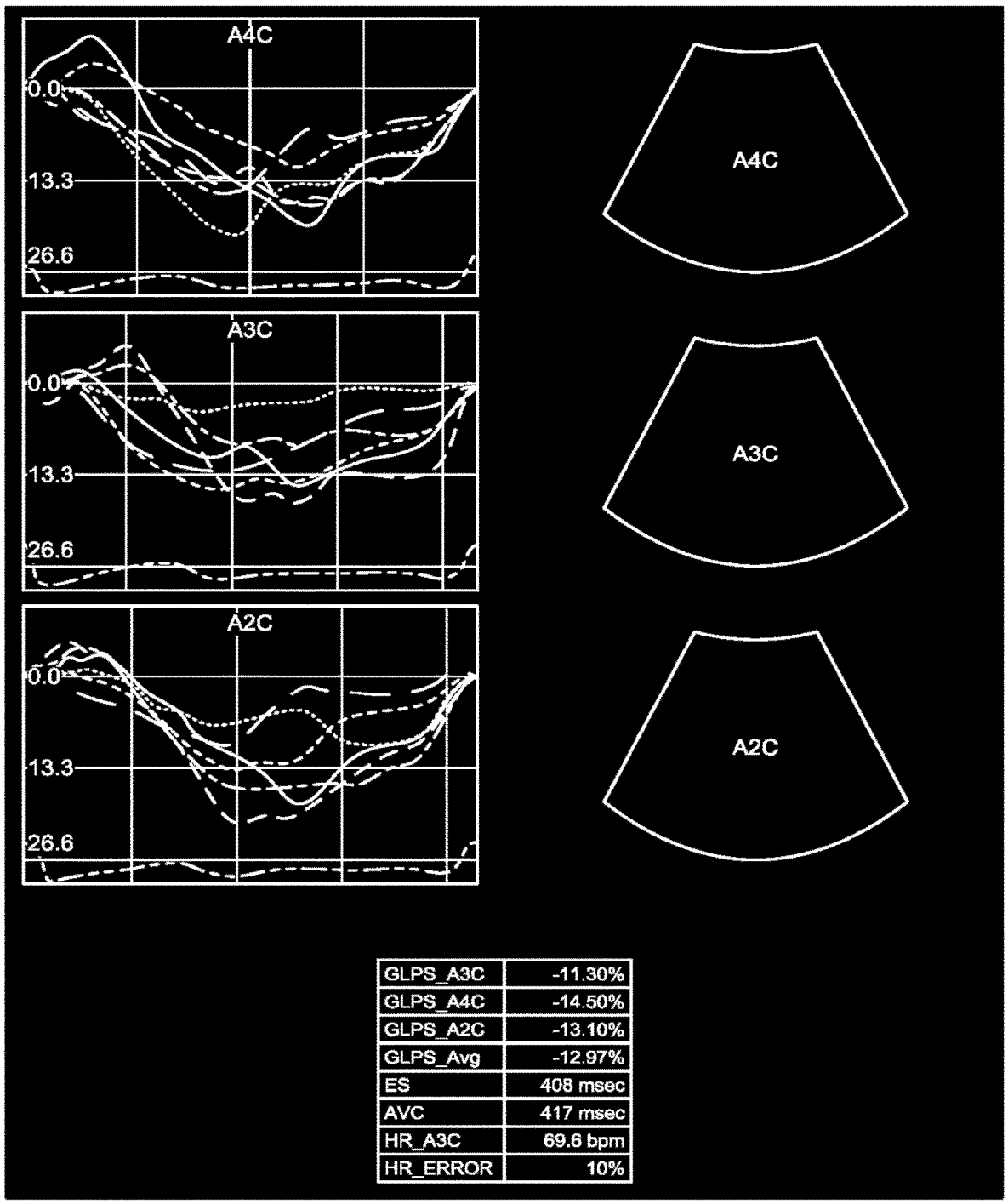
FIG. 15 is a diagram for explaining processing of a display control function according to a modification of the fourth embodiment.

FIG. 15 is a diagram for explaining processing of the display control function 173 according to a modification of the fourth embodiment. FIG. 15 exemplifies a display screen displayed on the display 103 by the processing of the display control function 173.

As illustrated in FIG. 15, the display control function 173 displays the time curves of the strain values of the cross sections (the graphs on the left side in FIG. 15) and the δHR(HR_ERROR) (the table at the bottom in FIG. 15). Furthermore, the display control function 173 causes an A4C image, an A3C image, and an A2C image (figures on the right side in FIG. 15). At this point, the pieces of image data of the cross sections may be for still images with an optional time phase or for moving images corresponding to the collection periods.

As described above, the ultrasonic diagnostic apparatus 1 according to the modification of the fourth embodiment can display the pieces of analysis information of the cross sections and an index value representing a difference in the cardiac cycle as well as the pieces of image data of the cross sections for which the tracking processing has been performed.

The details described in the above-described first to third embodiments may be applied to the fourth embodiment (or the modification of the fourth embodiment) except for displaying an index value representing a difference in the cardiac cycle.

Furthermore, the components of each device illustrated in the drawings are conceptual for describing functions, and not necessarily to be physically configured as illustrated in the drawings. In other words, specific forms of distribution and integration of the units are not limited to those illustrated in the drawings, and all or part of the units may be configured to be functionally or physically distributed and integrated in an arbitrary unit depending on various loads and conditions in use. Furthermore, all or an arbitrary part of processing functions performed by the respective units may be implemented by a CPU and a computer program to be analyzed and executed by the CPU, or implemented as hardware using wired logic.

Furthermore, out of the pieces of processing described in the embodiments above, all or part of the pieces of processing described as automatically performed may be performed manually. Alternatively, all or part of the pieces of processing described as performed manually may be performed automatically using a known technique. In addition, a procedure of processing, a procedure of control, a specific name, and information including various types of data and parameters that have been indicated in the descriptions above or in the drawings may be optionally changed unless specifically noted.

Furthermore, the image processing methods described in the embodiments above may be implemented by causing a computer such as a personal computer or a work station to execute an image processing programs prepared in advance.

These image processing methods may be distributed via a network such as the Internet. Furthermore, such an image processing method may be recorded in a computer-readable recording medium such as a flexible disk (FD), a CD-ROM, an MO, or a DVD and read out from the recording medium to be executed.

According to at least one embodiment described above, a polar coordinate display image can be displayed in a manner matching the time phases of the pieces of image data of a plurality of cross sections that have been separately collected.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising processing circuitry configured to
    with respect to pieces of image data of a plurality of cross sections passing through a heart of a subject that have been collected by individually ultrasonically scanning each of the cross sections for a period of at least one heart beat, perform tracking processing including two-dimensional pattern matching to generate pieces of analysis information in each of which a cardiac wall motion of the heart in each cross section is analyzed,
    match time phases at starting points of the image data of the cross sections without changing frame intervals of the image data of the cross sections,
    map the pieces of analysis information of the cross sections on a predetermined polar coordinate system based on the time phases of the cross sections with the matched starting points to generate a polar coordinate display image, and
    cause display of the polar coordinate display image.

2. The ultrasonic diagnostic apparatus according to claim 1, wherein the processing circuitry generates a strain value that represents a strain of the cardiac wall of the heart or an arrival time value with which the strain value arrives at a predetermined threshold as the pieces of analysis information.

3. The ultrasonic diagnostic apparatus according to claim 1, wherein the processing circuitry
    generates the pieces of analysis infonnation of the cross sections from the pieces of image data collected in different times of day, and
    matches the time phases of the pieces of analysis information of the cross sections in different times of day with a predetermined cardiac time phase as a reference.

4. The ultrasonic diagnostic apparatus according to claim 1, wherein the processing circuitry corrects the pieces of analysis information of the cross sections with a predetermined interval of a time between two cardiac time phases and maps the pieces of analysis information of the cross sections after correction on the predetermined polar coordinate system to generate the polar coordinate display image.

5. The ultrasonic diagnostic apparatus according to claim 1, wherein the processing circuitry performs interpolation processing such that time intervals of the pieces of analysis information of the cross sections are fixed time intervals based on a predetermined interval of a time between two cardiac time phases and maps pieces of analysis information out of the pieces of analysis information of the cross sections after correction with the same time phases on the polar coordinate system to generate the polar coordinate display image with a frame rate corresponding to the predetermined time intervals.

6. The ultrasonic diagnostic apparatus according to claim 5, wherein the processing circuitry causes display of the polar coordinate display image with a frame rate corresponding to the predetermined time intervals as a moving image.

7. The ultrasonic diagnostic apparatus according to claim 1, wherein the processing circuitry
generates the polar coordinate display image based on a piece of analysis information of a cross section, for which the wall motion analysis has been completed, out of the cross sections,
once the wall motion analysis operation for a cross section other than the cross section, for which the wall motion analysis has been completed, has been newly completed, updates the generated polar coordinate display image based on the piece of analysis information of the other cross section, and
every time the polar coordinate display image is updated, causes display of the updated polar coordinate display image.

8. The ultrasonic diagnostic apparatus according to claim 1, wherein the processing circuitry causes display of an index value representing a difference in cardiac cycles in collection periods of the cross sections.

9. The ultrasonic diagnostic apparatus according to claim 8, wherein the processing circuitry causes display of the index value when the index value has exceeded a threshold.

10. The ultrasonic diagnostic apparatus according to claim 8, wherein the processing circuitry generates a notification indicating that the index value has exceeded a threshold or causes display of the index value in an emphasized state when the index value has exceeded a threshold.

11. The ultrasonic diagnostic apparatus according to claim 1, wherein the cross sections are three cross sections of an apical two chamber, an apical three chamber, and an apical four chamber of the heart.

12. An image processing method, comprising:
with respect to pieces of image data of a plurality of cross sections passing through a heart of a subject that have been collected by individually ultrasonically scanning each of the cross sections for a period of at least one heart beat, performing tracking processing including two-dimensional pattern matching to generate pieces of analysis information in each of which a cardiac wall motion of the heart in each section is analyzed;
matching time phases at starting points of the image data of the cross sections without chancing frame intervals of the image data of the cross sections;
mapping the pieces of analysis information of the cross sections on a predetermined polar coordinate system based on the time phases of the cross sections with the matched starting points to generate a polar coordinate display image; and
causing display of the polar coordinate display image.

13. An ultrasonic diagnostic apparatus, comprising processing circuitry configured to
with respect to pieces of image data of a plurality of cross sections passing through a heart of a subject that have been collected by ultrasonically scanning each of the cross sections for a period of at least one heart beat, perform tracking processing including two-dimensional pattern matching to generate pieces of analysis information in each of which a cardiac wall motion of the heart in each cross section is analyzed,
match time phases of the pieces of analysis information of the cross sections and map the pieces of analysis information of the cross sections with the matched time phases on a predetermined polar coordinate system to generate a polar coordinate display image, and
cause display of the polar coordinate display image, wherein the processing circuitry generates the polar coordinate display image based on a piece of analysis information of a cross section, for which the wall motion analysis has been completed, out of the cross sections,
once the wall motion analysis operation for a cross section other than the cross section, for which the wall motion analysis has been completed, has been newly completed, updates the generated polar coordinate display image based on the piece of analysis information of the other cross section, and
every time the polar coordinate display image is updated, causes display of the updated polar coordinate display image.

* * * * *